(12) United States Patent
Smillie et al.

(10) Patent No.: US 12,109,284 B2
(45) Date of Patent: Oct. 8, 2024

(54) COMPOSITIONS COMPRISING FLUORIDE AND CALCIUM AND METHOD FOR PREPARING THEM

(71) Applicant: DENTHERAPY LTD, Aberdeen (GB)

(72) Inventors: David Andrew Smillie, Edinburgh (GB); Richard James Willson, Reading (GB)

(73) Assignee: DENTHERAPY LTD, Aberdeen (GB)

( * ) Notice: Subject to any disclaimer, the term of this patent is extended or adjusted under 35 U.S.C. 154(b) by 0 days.

(21) Appl. No.: 16/347,948

(22) PCT Filed: Nov. 7, 2017

(86) PCT No.: PCT/GB2017/053349
§ 371 (c)(1),
(2) Date: May 7, 2019

(87) PCT Pub. No.: WO2018/087532
PCT Pub. Date: May 17, 2018

(65) Prior Publication Data
US 2019/0274933 A1   Sep. 12, 2019

(30) Foreign Application Priority Data
Nov. 8, 2016   (GB) ..................... 1618826

(51) Int. Cl.
*A61K 8/24* (2006.01)
*A61K 8/19* (2006.01)
*A61K 8/64* (2006.01)
*A61Q 11/00* (2006.01)

(52) U.S. Cl.
CPC .................. *A61K 8/24* (2013.01); *A61K 8/19* (2013.01); *A61K 8/64* (2013.01); *A61Q 11/00* (2013.01); *A61K 2800/52* (2013.01); *A61K 2800/805* (2013.01); *A61K 2800/92* (2013.01)

(58) Field of Classification Search
CPC ............ A61Q 11/00; A61K 8/19; A61K 8/64; A61K 8/24; A61K 2800/52; A61K 2800/805; A61K 2800/92
See application file for complete search history.

(56) References Cited

U.S. PATENT DOCUMENTS

| 4,183,915 A * | 1/1980 | Gaffar | A61Q 11/00 424/52 |
| 6,652,875 B1 * | 11/2003 | Bannister | A61Q 11/00 424/440 |
| 9,295,628 B2 * | 3/2016 | Reynolds | A61Q 11/00 |

FOREIGN PATENT DOCUMENTS

| AU | 746314 | 9/1998 |
| AU | 2005309327 | 6/2006 |
| WO | WO9840406 | 9/1998 |
| WO | WO0149741 | 7/2001 |
| WO | WO0228413 | 4/2002 |
| WO | WO2006050013 | 5/2006 |
| WO | 2006056013 | 6/2006 |
| WO | WO2006135982 | 12/2006 |
| WO | WO2012117119 | 9/2012 |
| WO | WO2012117120 | 9/2012 |
| WO | WO2013144247 | 10/2013 |
| WO | WO02016101041 | 6/2016 |

OTHER PUBLICATIONS

Gericke et al., "Importance of Phosphorylation for Osteopontin Regulation of Biomineralization", Calcified Tissue International, 77, pp. 45-54 (Year: 2005).*
Gericke A, Qin C, Spevak L, Fujimoto Y, Butler W T, Sørensen E S, Boskey A L, Importance of Phosphorylation for Osteopontin Regulation of Biomineralization, vol. 77, Nr:1, pp. 45-54, Publication info: XP019362722.
International Search Report, for International Application No. PCT/GB2017/053349; Jan. 10, 2018.
Reynolds, E.C.; Remineralization of Enamel Subsurface Lesions by Casein Phosphopeptide-stablized Calcium Phosphate Solutions; Journal of Dental Research; Sep. 1997; 1587-1595; J Den Res 76(9); Melbourne, Australia.

* cited by examiner

*Primary Examiner* — Lezah Roberts
(74) *Attorney, Agent, or Firm* — Dickinson Wright PLLC

(57) ABSTRACT

The present invention relates to methods for preparing compositions comprising calcium and fluoride, and, in particular, to methods for preparing compositions comprising calcium that is stabilised with a stabilising agent and fluoride. For example, the method is for the preparation of compositions comprising amorphous calcium phosphate stabilised by phosphopeptides, and free fluoride. The invention also extends to various compositions produced by such methods, including oral care products.

20 Claims, 5 Drawing Sheets

COMPOSITIONS COMPRISING FLUORIDE AND CALCIUM AND METHOD FOR PREPARING THEM

CROSS-REFERENCE TO RELATED APPLICATIONS

The present application is a Section 371 National Stage of International Application PCT/GB2017/053349, filed 7 Nov. 2017, and through which priority is claimed to UK Patent Application 1618826.0, filed 8 Nov. 2016.

The present invention relates to methods for preparing compositions comprising calcium and fluoride. In particular, the present invention relates to methods for preparing compositions comprising calcium that is stabilised with a stabilising agent and fluoride. For example, the method is for the preparation of compositions comprising amorphous calcium phosphate stabilised by phosphopeptides, and free fluoride. The invention also extends to various compositions produced by such methods, including oral care products.

BACKGROUND OF THE INVENTION

Dental enamel and dentine is subject to processes of demineralisation, characterised by loss of calcium and phosphate from the porous tooth surface, and remineralisation whereby the actions of saliva restore the hydroxyapatite of the tooth enamel. When the rate of demineralisation is greater than remineralisation, in the early phase, demineralisation causes the softening of the enamel making it susceptible to enamel loss. Progression from early phase demineralisation can result in cariogenic lesion or dental erosion. Enamel erosion and dental caries is typically caused by the demineralisation of dental enamel, typically by organic acids produced from fermentation of dietary sugar by dental plaque bacteria or from acid foods or drink, or from intrinsic acids during gastric reflux or bulimia nervosa.

Tooth enamel consists mostly of calcium hydroxyphosphate, $Ca_5(PO_4)_3OH$ (also known as hydroxyapatite). Hydroxyapatite is a hard, insoluble compound, but acid in the mouth (e.g. from dental plaque bacteria) breaks down the apatite. The chemical reaction is as follows: $Ca_{10}(PO_4)_6(OH)_2 + 8H^+ = 10Ca^{2+} + 6HPO_4^{2-} + 2H_2O$ (See, "On the Dissolution of Hydroxyapatite in Acid Solutions": J. Dent. Res. 1988, 76, 1056).

In an acidic environment (i.e. at a pH below the pka of hydroxyapatite) the enamel will begin the process of dissolution where calcium, phosphate and hydroxyl groups will become ionised and solvated by the surrounding solvent. The process is an equilibrium between the calcium, phosphate and hydroxide molecules in a solid crystal lattice and the corresponding ions in solution. The position of the equilibrium is dictated by: the pKa of the dissolving apatite, the pH of the solution and by the concentration of the ions in solution.

The addition of fluoride to the composition has the advantage of inducing a chemical modification of enamel from calcium hydroxyl apatite to calcium fluorapatite and so change the position of the dissolution equilibrium to favour the solid form of apatite. In addition the availability of fluoride ions act as a catalyst to promote the remineralisation of eroded enamel.

Fluorapatite resists attacks by acids better than hydroxyapatite itself, so the tooth enamel resists decay better than enamel containing no fluoride.

Thus, it is known that remineralisation can be enhanced by inclusion of a source of fluoride ions in dental care formulae. It is also known that delivery of bioavailable calcium and phosphate ions to the enamel surface enhances remineralisation by changing the position of the equilibrium to favour the apatite crystalline form. However, these ions are prone to forming insoluble salts upon mixing in aqueous solution. Therefore, a simple solution containing calcium, phosphate and fluoride will react with itself to form an insoluble calcium fluoride solid that is not biologically active.

WO1998/040406 and WO2006/050013 teach that soluble complexes of amorphous calcium phosphate (ACP) or amorphous calcium phosphate fluoride (ACPF), stabilised by phosphopeptides containing the amino acid sequence Ser(P)-Ser(P)-Ser(P)-Glu-Glu, may be formed by admixing of solutions of calcium, phosphate and fluoride ions with solutions of phosphopeptides at pH levels above or below neutral respectively. Such preparations are suitable for inclusion in medicaments for the prevention or treatment of dental cariogenic conditions by delivering bioavailable ACP or ACPF to the enamel surface. WO2006/135982 teaches that phosphopeptide stabilised ACP or ACPF can be 'superloaded' with calcium and phosphate ions by mixing purified stabilised complexes with a suitable source of calcium and phosphate ions for the production of medicaments intended to prevent or treat dental caries.

The present invention addresses the stability and availability of fluoride in calcium containing compositions by means that do not depend upon intermediate formulation steps or the addition of calcium chelating agents to the formulation.

STATEMENTS OF THE INVENTION

According to a first aspect, the present invention provides a method of preparing a liquid composition comprising stabilised amorphous calcium phosphate and fluoride, the method comprising:
   a) providing a source of calcium ions, a source of phosphate ions, a calcium phosphate-stabilising agent, and monofluorophosphate;
   b) mixing said source of calcium ions and source of phosphate ions together with the calcium phosphate-stabilising agent in a liquid medium in order to form a stabilised amorphous calcium phosphate complex; and
   c) mixing the monofluorophosphate with the source of calcium ions, source of phosphate ions, calcium phosphate-stabilising agent and/or stabilised amorphous calcium phosphate complex in the liquid medium;
   thereby producing a liquid composition comprising stabilised amorphous calcium phosphate and fluoride.

It has surprisingly been found that, by preparing a composition according to the method of the invention, a liquid composition with beneficial properties can be formed in a remarkably efficient manner. In particular, the method of the present invention allows the convenient preparation of a composition that comprises amorphous calcium phosphate and free fluoride. "Free fluoride" in this context can be viewed as fluoride ions in solution.

The method of the present invention allows the production of a liquid composition in which calcium is stabilised in a complex, and wherein fluoride is introduced during the manufacturing process in such a way that calcium and fluoride molecules are largely prevented from interacting with each other and forming stable but insoluble calcium fluoride, which forms a precipitate. The product obtained is thus able to deliver both fluoride and calcium ions when applied to, for example, a tooth surface. On application, the composition provides the active components, calcium, fluoride and phosphates, in a way that is efficacious in the repair of enamel and for the protection from damage to enamel when subjected to an acid challenge. Without wishing to be bound by theory, the efficacy of the method of the present invention is believed to be a result of the interplay between the kinetics for the structuring of calcium ions within the stabilized complex, and the delayed and gradual release of fluoride ions from monofluorophosphate. This results in the situation where free calcium ions do not have any significant opportunity to react with free fluoride ions.

In a preferred embodiment, the monofluorophosphate is mixed with the source of calcium ions, source of phosphate ions, and calcium phosphate-stabilising agent before formation of the stabilised calcium phosphate complex has completed or has reached an equilibrium point. As discussed above, it is a feature of the present invention that the monofluorophosphate only gradually releases free fluoride ions, and as such it is possible to mix monofluorophosphate with a source of calcium ions without the formation of significant amounts of calcium fluoride. In contrast, should a source of fluoride that releases fluoride ions rapidly, e.g. a soluble fluoride salt, be provided before formation of the stabilised calcium phosphate complex has completed, significant amounts of calcium fluoride would be prepared, and an undesirable composition would be formed, i.e. one containing significant amounts of calcium fluoride precipitate, and lacking in stabilised calcium phosphate.

Accordingly, in a preferred embodiment of the invention, the monofluorophosphate, source of calcium ions, source of phosphate ions, and calcium phosphate-stabilising agent are mixed together in a single reaction. In this embodiment the relevant ingredients are brought together at effectively the same time, e.g. in a single mixing process, such that they react together. Mixing all of these ingredients together to utilise a single reaction approach has significant advantages in terms of simplicity and efficiency of the manufacturing process. This can be contrasted to the situation where a source of fluoride, e.g. a soluble fluoride salt, is added in a later, separate reaction, i.e. once the formation of stable calcium phosphate complexes had completed.

In a preferred embodiment, a 'single reaction' in the present context can be defined as a process whereby the monofluorophosphate, source of calcium ions, source of phosphate ions, and calcium phosphate-stabilising agent are added to a single reaction vessel with the liquid medium and mixed together and allowed to react together. The reactants can be added sequentially or simultaneously; in some cases they are added sequentially for practical reasons. Where the ingredients are added sequentially, it is sometimes preferable that the monofluorophosphate is added after the source of calcium ions, source of phosphate ions, and calcium phosphate-stabilising agent; for example, it can suitably be the final ingredient to be added.

Suitably the ingredients are all added within a relatively short period of time. The period can in some cases be dictated by the efficiency of the mixing of the calcium chloride. The efficiency of mixing can be important to prevent significant concentration gradients of calcium occurring, that could, in some cases, lead to precipitation of insoluble calcium salts. The person skilled in the art can readily select suitable conditions and addition rates for any given mixing process. Mixing can be achieved, for example, by stirring of the mixture, but many other mixing processes can be used.

Thus, in a preferred embodiment of the invention, the method is performed in a reaction having a mixing step in which the monofluorophosphate, the source of calcium ions, the source of phosphate ions, and the calcium phosphate-stabilising agent are mixed together at substantially the same time. In other words, steps b) and c) of the method above are performed together in a single reaction.

Suitably the method comprises storing the liquid composition under suitable conditions for monofluorophosphate to decompose to release free fluoride into the liquid medium. This will occur under standard storage conditions, e.g. room temperature, but other storage conditions could be used as required.

Any suitable source of calcium ions can be used. The source of calcium ions should be able to dissolve in the liquid medium to release calcium ions for use in forming the stabilised calcium phosphate complex. Preferably the source of calcium ions is a soluble calcium salt. Suitably the source of calcium ions has a solubility of 5 g per 100 ml of liquid medium or higher, preferably 10 g per 100 ml of liquid medium or higher, yet more preferably 50 g per 100 ml of liquid medium or higher. The source of calcium ions can be provided in solid form or be dissolved in a suitable liquid.

One particularly suitable source of calcium ions is calcium chloride, but the person skilled in the art can select many other suitable sources of calcium ions.

Any suitable source of phosphate ions can be used. The source of calcium ions should be able to dissolve in the liquid medium to release phosphate ions for use in forming the stabilised calcium phosphate complex. Preferably the source of phosphate ions is a soluble phosphate salt. Suitably the source of phosphate ions has a solubility of 5 g per 100 ml of liquid medium or higher, preferably 10 g per 100 ml of liquid medium or higher, yet more preferably 50 g per 100 ml of liquid medium or higher. The source of phosphate ions can be provided in solid form or be dissolved in a suitable liquid.

One particularly suitable source of phosphate ions is sodium phosphate (suitably disodium hydrogen phosphate and/or trisodium phosphate), but the person skilled in the art can select many other suitable sources of phosphate ions.

When discussing the solubility of a composition, it is meant solubility at 25° C. (and otherwise standard conditions) in the relevant liquid medium used in the method. Typically, this medium will be aqueous, and in some cases will be water. It will be appreciated that the solubility of a given composition will vary depending on the relevant medium being used, e.g. depending on its polarity, but in the context that is entirely appropriate as the compositions such as calcium or phosphate salts are preferably soluble in the relevant medium being used. However, given that the medium is typically aqueous, it may be more convenient and simple to define the solubility in terms of solubility in water. Accordingly, solubility of the source of calcium or phosphate ions is suitably of 5 g per 100 ml of water or higher, preferably 10 g per 100 ml of water or higher, yet more preferably 50 g per 100 ml of water or higher.

A "calcium phosphate-stabilising agent" is an agent that is capable of binding to and stabilising calcium phosphate in a stabilised calcium phosphate complex. Preferably the calcium phosphate is stabilised as amorphous calcium phosphate.

A "stabilised calcium phosphate complex" is a complex comprising calcium, phosphates and the calcium phosphate-stabilising agent. The stabilised complex is preferably soluble or at least metastable in the liquid medium in which it is contained, i.e. the liquid composition. As discussed below, calcium phosphate-stabilising agents (such as phosphopeptides) are able to bind to calcium phosphate complexes and prevent them from precipitating. In particular, amorphous calcium phosphate complexes can be stabilised in form in which they remain soluble (or metastable) and are able to release calcium and phosphate.

In preferred embodiments of the present invention, the calcium phosphate-stabilising agent comprises a phosphoprotein or phosphopeptide. A range of phosphoproteins and phosphopeptides that are able to interact with and stabilise calcium phosphate are well-known in the art. In particular, mention can be made of osteopontin or phosphopeptides derived therefrom, and casein or phosphopeptides derived therefrom. These two proteins and their phosphopeptides have been extensively discussed in the literature in respect of forming stabilised calcium phosphate complexes. However, there are other phosphoproteins and phosphopeptides which can form stabilised calcium phosphate complexes, such as phosvitin (Swiss-Prot Accession No P67869), fetuin A (FETUA) (Swiss-Prot Accession No P02765), proline-rich basic phosphoprotein 4 (PRB4) (Swiss-Prot Accession No PI 0163), matrix Gla protein (MGP) (Swiss-Prot Accession No P08493), secreted phosphoprotein 24 (SPP-24) (Swiss-Prot Accession No Q13103), Riboflavin Binding Protein (Swiss-Prot Accession No P02752), integrin binding sialophosphoprotein II (IBSP-II) (Swiss-Prot Accession No P21815), matrix extracellular bone phosphoglycoprotein (MEPE) (Swiss-Prot Accession No Q9NQ76), dentin matrix acidic phosphoprotein 1 (OMP1) (Swiss-Prot Accession No Q13316), human beta-casein, bovine beta-casein, and isoforms or phosphopeptides derived therefrom. Moreover, there are potentially a wide range of synthetic phosphoproteins and phosphopeptides that can be used in the present invention.

Thus, suitable phosphoproteins and phosphopeptides may be from any source and take a number of forms. For example, suitable phosphoproteins and phosphopeptides include full length phosphoproteins, or phosphopeptides derived therefrom that may be naturally occurring or may be formed or isolated by tryptic or chemical (e.g. alkaline hydrolysis) digestion of such phosphoproteins, or obtained by chemical or recombinant synthesis. The phosphoproteins or phosphopeptides may be osteopontin or casein, or may be derived from osteopontin, casein, or other phosphoamino acid rich proteins such as phosvitin (Swiss-Prot Accession No P67869), fetuin A (FETUA) (Swiss-Prot Accession No P02765), proline-rich basic phosphoprotein 4 (PRB4) (Swiss-Prot Accession No PI 0163), matrix Gla protein (MGP) (Swiss-Prot Accession No P08493), secreted phosphoprotein 24 (SPP-24) (Swiss-Prot Accession No Q13103), Riboflavin Binding Protein (Swiss-Prot Accession No P02752), integrin binding sialophosphoprotein II (IBSP-II) (Swiss-Prot Accession No P21815), matrix extracellular bone phosphoglycoprotein (MEPE) (Swiss-Prot Accession No Q9NQ76), dentin matrix acidic phosphoprotein 1 (OMP1) (Swiss-Prot Accession No Q13316), human beta-casein, bovine beta-casein, and isoforms or phosphopeptides derived therefrom.

Phosphopeptides obtained by enzymatic (e.g. tryptic) digest of osteopontin or casein are particularly preferred calcium phosphate-stabilising agents for use in the present invention.

Osteopontin (OPN) is a protein that can be obtained from milk. For example, bovine OPN can be isolated by anion exchange chromatography from e.g. acid whey at pH 4.5 as described by the patent applications WO 01/497741 A2, WO 02/28413, WO 2012/117,119 or WO 2012/117,120. An OPN purity of up to 90-95% can be obtained. The present invention can use naturally occurring fragments or peptides derived from OPN by proteolytic cleavage in the milk, or genesplice-, phosphorylation-, or glycosylation variants as obtainable from the method proposed in, for example, WO 01/49741 and WO2013/144247. OPN can be derived from milk from any milk producing animals, such as cows, humans, camels, goats, sheep, dromedaries and llamas. OPN from bovine milk is typically preferred due to availability and characterisation in the literature. OPN is present in bovine milk, both in the form of full length bovine OPN (e.g. position 17-278 of Swiss-Prot Accession No P31096, or a peptide having at least 95% sequence identity with position 17-278 of Swiss-Prot Accession No P31096) and in the form of a long N-terminal fragment of full length bovine OPN (e.g. position 17-163 of Swiss-Prot Accession No P31096, or a peptide having at least 95% sequence identity with position 17-163 of Swiss-Prot Accession No P31096), see e.g. Bissonnette et al., Journal of Dairy Science Vol. 95 No. 2, 2012). Full length OPN is an acidic, highly phosphorylated, sialic acid rich, calcium binding protein. Full length osteopontin binds 28 moles of phosphate and about 50 moles of Ca per mole. The use of OPN to form calcium phosphate complexes is discussed extensively in, for example, WO2013/144247, particularly but not exclusively in respect of their use to treat biofilm related diseases.

In some embodiments of the invention, the OPN or phosphopeptides derived therefrom may be substantially pure full length bovine OPN, it may be a substantially pure, long N-terminal fragment of full length bovine OPN, and it may be a mixture comprising full length bovine OPN and the long N-terminal fragment of full length bovine OPN. Such a mixture may for example contain full length bovine OPN in an amount of 5-40% (w/w) relative to the total amount of OPN and the long n-terminal fragment of full length bovine OPN in an amount of 60-95% (w/w) relative to the total amount of OPN.

Phosphopeptides derived from OPN (e.g. by the cleavage of OPN, such as by tryptic or chemical (e.g. alkaline hydrolysis) digestion of OPN), are particularly preferred for use in the present invention. For example, OPN-derived phosphopeptides sold commercially as Lacprodan® OPN-10 form suitable and preferred examples of phosphopeptides derived from OPN for use in the present invention. OPN-10 is available commercially from Arla Foods Ingredients (Arla Foods Ingredients Group P/S, Søinderhøj 10-12, 8260 Viby J, Denmark), and contains fractionated osteopontin from bovine milk.

Casein and casein-derived phosphopeptides are discussed at length in WO 98/40406 and WO 2006/135982, and these phosphoproteins and phosphopeptides can suitably be used in the present invention. Accordingly, the method of the present invention may use casein phosphoproteins or casein phosphopeptides (CPP).

As discussed in WO 2006/135982, CPP can form a colloidal complex with amorphous calcium phosphate, where the core particles aggregate to form large (e.g. 100 nm) colloidal particles suspended in water. It is believed that this general method of stabilisation of calcium phosphate stabilisation also occurs for other phosphoproteins. Without wishing to be bound by theory, the phosphopeptide seems to bind to an amorphous calcium phosphate (ACP) cluster to produce a metastable solution in which growth of ACP to a size that initiates nucleation and precipitation is prevented.

Phosphopeptides comprising the motif Ser(P)-Ser(P)-Ser(P)-Glu-Glu, which is present in casein phosphopeptides, are preferred in some embodiments of the present invention. However, phosphopeptides other sequence motifs rich in phosphoamino acids are also of use in the present invention.

Casein-derived phosphopeptides comprising the sequences $\alpha_{s1}(59\text{-}79)$, $\beta(1\text{-}25)$, $\alpha_{s2}(46\text{-}70)$ and $\alpha_{s1}(1\text{-}21)$, as set out in WO 98/40406 and WO 2006/135982, are preferred casein phosphopeptides for some embodiments of the present invention. Additional flanking sequences surrounding these core sequences may be present, in which case they can be wild type sequences or may optionally be modified by deletion, addition or conservative substitution of one or more residues.

Accordingly, in preferred embodiments of the present invention, the calcium phosphate-stabilising agent comprises osteopontin or phosphopeptides derived therefrom, or casein or phosphopeptides derived therefrom. Yet more preferably, the calcium phosphate-stabilising agent comprises osteopontin-derived phosphopeptides or casein-derived phosphopeptides.

Alternatively or additionally, the calcium phosphate-stabilising agent can suitably comprise one or more phosphoproteins selected from the group consisting of phosvitin (Swiss-Prot Accession No P67869), fetuin A (FETUA) (Swiss-Prot Accession No P02765), proline-rich basic phosphoprotein 4 (PRB4) (Swiss-Prot Accession No PI 0163), matrix Gla protein (MGP) (Swiss-Prot Accession No P08493), secreted phosphoprotein 24 (SPP-24) (Swiss-Prot Accession No Q13103), Riboflavin Binding Protein (Swiss-Prot Accession No P02752), integrin binding sialophosphoprotein II (IBSP-II) (Swiss-Prot Accession No P21815), matrix extracellular bone phosphoglycoprotein (MEPE) (Swiss-Prot Accession No Q9NQ76), dentin matrix acidic phosphoprotein 1 (OMP1) (Swiss-Prot Accession No Q13316), human beta-casein, bovine beta-casein, and isoforms or phosphopeptides derived therefrom.

For the avoidance of doubt, it should be noted that in embodiments of the present invention, the calcium phosphate-stabilising agent can comprise a mixture of different phosphopeptides and/or phosphoproteins. For example, the calcium phosphate-stabilising agent may comprise a mixture of different phosphopeptides derived from a single phosphoprotein (e.g. casein or OPN). Alternatively, the calcium phosphate-stabilising agent may comprise a mixture of different phosphoproteins (e.g. a mixture of casein and OPN, or other different phosphoproteins) and/or phosphopeptides derived from a mixture of more than one different phosphoprotein (e.g. a mixture of phosphopeptides derived from both casein and OPN). In many cases, the calcium phosphate-stabilising agent used in the present invention will comprise a heterogeneous mixture of phosphopeptides obtained by the cleavage of a naturally occurring protein, such as OPN or casein.

It is generally preferred that the liquid composition formed in the method of the present invention is an aqueous composition. Accordingly, it is preferred that the liquid medium is an aqueous medium. More preferably the liquid medium is water. Suitably the aqueous composition comprises at least 50% v/v water, optionally at least 75% v/v water or at least 90% v/v water.

In some preferred embodiments, the liquid composition comprises a pH buffering agent (or buffer). Various pH buffering agents are well-known to the skilled person. Exemplary buffers include, but are not limited to, phosphate buffers, Tris (tris(hydroxymethyl)aminomethane) buffers, and sodium bicarbonate. Preferably the pH buffering agent is suitable to maintain the liquid solution at a pH of above 7, more preferably in the range of from pH 7 to 9, yet more preferably pH 7.1 to 8.5, yet more preferably pH 7.2 to 8. Preferably said pH is maintained for a period of storage at room temperature of at least 6 weeks, preferably 3 months, more preferably 6 months, and yet more preferably at least 1 year. Suitable buffering agents to achieve this will be apparent to the skilled person and their suitability for purpose can be readily determined experimentally. Accordingly, in preferred embodiments, the method comprises addition of a pH buffering agent. The pH buffering agent can be added at any suitable point in the method.

The liquid composition may comprise other liquid or soluble components such as one or more of alcohol(s) (e.g. ethanol), humectant(s), surfactant(s), preservative(s), flavouring agent(s), sweetening agent(s), colouring agent(s), and anti-caries agent(s) other than the stabilised calcium phosphate and fluoride provided by the above method. Accordingly, the method may comprise providing one or more of the above-mentioned components in the liquid composition. Such components can be present in the liquid medium ab initio or added to the composition before, at the same time as, or after the source of calcium ions, the source of phosphate ions, the calcium phosphate-stabilising agent, and/or the monofluorophosphate.

The method can suitably be carried out a room temperature and at standard atmospheric conditions. Other conditions can be used, if required.

The amounts of the various components of the compositions of the present invention can of course be determined by the person skilled in the art. As a general rule, there should be sufficient calcium phosphate-stabilising agent and source of phosphate ions to ensure that substantially all calcium present in the medium is incorporated into calcium phosphate and preferably into stabilised complexes. Otherwise, free calcium will tend to react with free fluoride to form calcium fluoride. Whether this is the case or not can readily be determined via routine experimentation, with the production of significant amounts of insoluble calcium fluoride precipitate being indicative of insufficient calcium phosphate-stabilising agent and/or source of phosphate ions.

In embodiments of the present invention, the components of the composition are suitably provided in the following amounts:

water—from about 50% to about 99% by weight; preferably from about 75% to about 99% by weight;

source of calcium ions (e.g. a soluble calcium salt or other options as discussed above)—from about 0.1% to about 15% by weight; preferably from about 0.1% to about 5% by weight, suitably from about 0.2% to about 1% by weight, e.g. from 0.4 to 0.5% by weight.

source of phosphate ions (e.g. a soluble phosphate salt or other options as discussed above)—from about 0.2% to about 15% by weight; preferably from about 0.5% to about 5% w/v, suitably from about 0.7% to about 2% by weight, e.g. from 0.8 to 1.2% by weight.

calcium phosphate-stabilising agent (e.g. phosphopeptides or other options as discussed above)—from about 0.5% to about 15% w/v; preferably from about 1% to about 10% by weight, suitably from about 1.5% to about 5% by weight, e.g. from 2 to 4% by weight.

monofluorophosphate—from about 0.05% to about 3%; preferably from about 0.1% to about 1.5% by weight, suitably from about 0.15% to about 1% by weight, e.g. from 0.2% to 0.6% by weight; and flavouring, preservative and/or other ingredients from about 0% to about 20% by weight.

Preferably the composition also comprises a pH buffering agent, as discussed above.

It will be apparent to the skilled person that suitable proportions of the above components can be selected and added during the method to give the desired total amount.

One exemplary composition of the present invention comprises:
Water 46.47 mols dm$^{-3}$ (87.47% w/v);
OPN-10 (3% w/v);
Calcium chloride 28.821 mmols dm-3 (0.42% w/v);
Phosphate ions 0.032 mols dm-3 (1.03% w/v);
MFP 0.026 mols/dm-3 (0.38% w/v);
Flavouring (6.7% w/v); and
Preservative (1% w/v).

Thus, the ingredients are suitably added in appropriate quantities to give these amounts in the final composition.

In preferred embodiments of the present invention, the liquid composition is an oral spray or mouthwash. Accordingly, the method suitably comprises the additional step of formulation the liquid composition as an oral spray or mouthwash. Such oral sprays or mouthwashes typically comprise an aqueous liquid medium. It is generally preferred that no alcohol is present in the aqueous liquid medium, but in some cases it can comprise an alcohol. Generally, where alcohol is present, the weight ratio of water to alcohol is in the range of from about 1:1 to about 20:1. The total amount of water-alcohol mixture in this type of preparation is typically in the range of from about 70 to about 99.9% by weight of the preparation. The alcohol is typically ethanol or isopropanol, with ethanol being preferred.

Mouth washes and mouth sprays according to the present invention can suitably include the following exemplary components by weight:
water (suitably from about 45% to about 95%),
ethanol (suitably from about 0% to about 25%),
humectant(s) (suitably from about 0% to about 50%),
surfactant(s) (suitably from about 0.01% to about 7%),
flavouring agent(s) (suitably from about 0.04% to about 2%),
sweetening agent(s) (suitably from about 0.1% to about 8%),
colouring agent(s) (suitably from about 0% to about 0.5%),
xylitol (suitably from about 0% to about 8%),
anti-caries agent(s), including but not limited to stabilised calcium phosphate and fluoride (suitably from about 0.001% to 10%), and optionally
an anti-calculus agent (suitably from about 0% to about 13%).

Thus, the ingredients are suitably added in appropriate quantities to give these amounts in the final composition. Examples of these components are well known to the skilled person.

In preferred embodiments of the present invention the final pH of the liquid composition is greater than 7. The final pH in this case relates to the pH which is achieved after a period of storage sufficient to allow formation of the stabilised calcium phosphate complex to substantially complete or substantially reach an equilibrium point.

The method may include the step of adjusting the pH of the composition. The pH may be adjusted by the addition of hydrogen ions (acid) or hydroxide ions (base), as required. Any physiologically compatible or acceptable acid or base may typically be used, e.g. hydrochloric acid and NaOH.

As mentioned above, a pH buffer may be used to maintain the pH at the desired level, e.g. phosphate buffer, Tris (tris(hydroxymethyl)aminomethane) buffer, and sodium bicarbonate. Thus, the method may include adding a pH buffer.

The method may further comprise the step of combining the liquid composition of the present invention with one or more additional compositions or carriers. For example, the liquid composition can be combined with suitable well-known components to form an oral care product; for example, a toothpaste, cream or gel, chewing gum, powder or granules, wafer tabs, delivery strips, tablets, capsules or the like. The liquid composition can suitably be mixed with, adsorbed to, absorbed by, or encapsulated within the one or more additional compositions or carriers. Additional compositions or carriers used in such products are well known in the art. The method may thus be a method of producing an oral care product and comprise the step of combining the liquid composition produced by the above steps with additional compositions or carriers to form an oral care product.

In a second aspect, the present invention provides a liquid composition or oral care product comprising stabilised calcium phosphate and fluoride obtained by the method as set out above.

In one embodiment the composition suitably comprises the following ingredients in the specified amounts:
water—from about 50% to about 99% by weight; preferably from about 75% to about 99% by weight;
source of calcium ions (e.g. a soluble calcium salt or other options as discussed above)—from about 0.1% to about 15% by weight; preferably from about 0.1% to about 5% by weight, suitably from about 0.2% to about 1% by weight, e.g. from 0.4 to 0.5% by weight.
source of phosphate ions (e.g. a soluble phosphate salt or other options as discussed above)—from about 0.2% to about 15% by weight; preferably from about 0.5% to about 5% w/v, suitably from about 0.7% to about 2% by weight, e.g. from 0.8 to 1.2% by weight.
calcium phosphate-stabilising agent (e.g. phosphopeptides or other options as discussed above)—from about 0.5% to about 15% w/v; preferably from about 1% to about 10% by weight, suitably from about 1.5% to about 5% by weight, e.g. from 2 to 4% by weight.
monofluorophosphate—from about 0.05% to about 3%; preferably from about 0.1% to about 1.5% by weight, suitably from about 0.15% to about 1% by weight, e.g. from 0.2% to 0.6% by weight; and
flavouring, preservative and/or other ingredients from about 0% to about 20% by weight.

An exemplary composition of the present invention comprises:
Water 46.47 mols dm$^{-3}$ (87.47% w/v);
OPN-10 (3% w/v);
Calcium chloride 28.821 mmols dm-3 (0.42% w/v);
Phosphate ions 0.032 mols dm-3 (1.03% w/v);
MFP 0.026 mols/dm-3 (0.38% w/v);
Flavouring (6.7% w/v); and
Preservative (1% w/v).

Preferably the composition is an oral spray or mouthwash. Exemplary mouthwash and spray formulations are set out above. Alternatively, the composition may be in the form of an oral care product such as a toothpaste, cream or gel, chewing gum, powder or granules, wafer tabs, delivery strips, tablets, capsules or the like, in which the oral care product incorporated the liquid composition.

In a further aspect, the present invention provides an oral care product, particularly but not exclusively an oral spray or mouthwash, comprising a liquid composition comprising stabilised amorphous calcium phosphate and fluoride obtained according to the method as set out above.

In a further aspect, the present invention provides a method of treating or preventing a dental disease or a dental condition, e.g. a dental condition or disease involving dental demineralisation (e.g. dental erosion or dental caries) by administering a composition according to the present invention to the oral cavity of a subject, e.g. a human.

In a further aspect, the present invention provides a composition according to the present invention for use in the treatment or prevention of a dental disease or a dental condition, e.g. a dental condition or disease involving dental demineralisation (e.g. dental erosion or dental caries), by administering a composition according to the present invention to the oral cavity of a subject, e.g. a human.

In a further aspect of the present invention there is provided a liquid composition comprising amorphous calcium phosphate stabilised by a calcium phosphate-stabilising agent and monofluorophosphate. Various preferred features of this aspect are described above in respect of the above aspects of the invention.

Embodiments of the present invention will now be described, by way of non-limiting example, with reference to the accompanying drawings.

SPECIFIC DESCRIPTION OF EMBODIMENTS OF THE INVENTION

Figure 1:
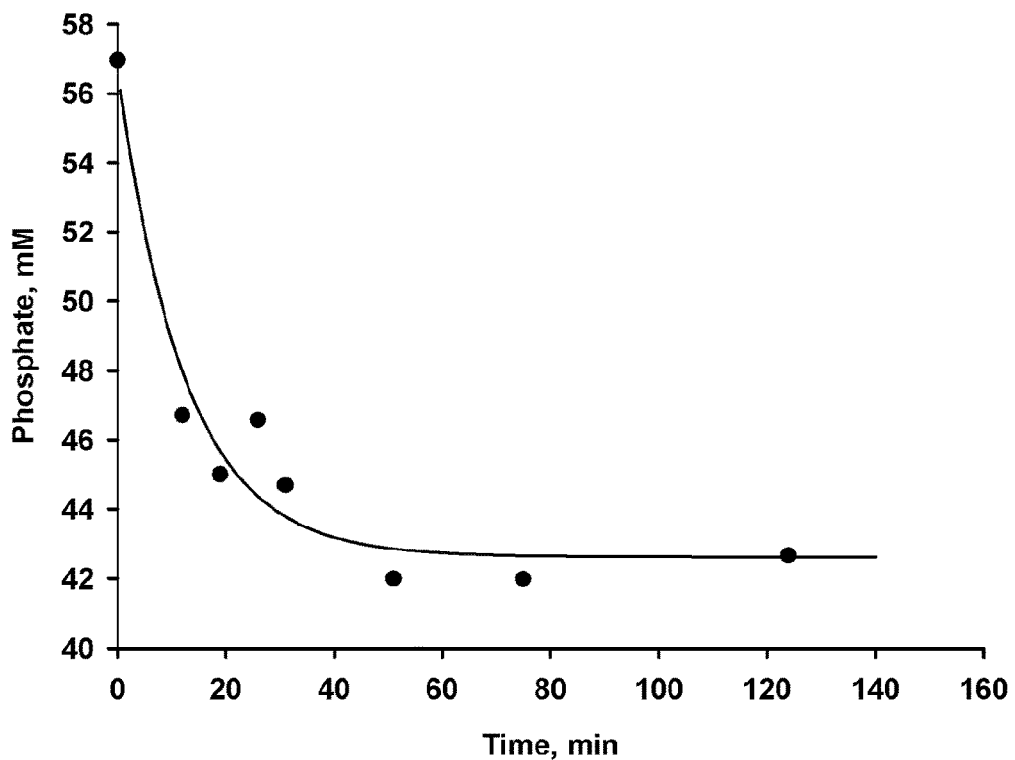
FIG. 1—Mineralisation of HA powder by a 4% OPN-10 formulation containing 69 mM phosphate.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

Terms used herein have meanings as commonly understood by a person of ordinary skill in the areas relevant to the present invention unless another meaning is specifically defined or dictated by the context. Terms such as "a", "an" and "the" are not intended to refer to only a singular entity, but include the general class of which a specific example may be used for illustration. The terminology used hereinbelow is used to describe specific embodiments of the invention, but their usage does not delimit the invention, except as outlined in the claims.

Example 1—Formulation and Manufacture of a Composition Comprising Osteopontin Phosphopeptide (OPN-10) Stabilised Amorphous Calcium Phosphate Described below is a manufacturing procedure for a composition according to the present invention, the composition comprising 3% OPN-10 (w/w) with a flavouring agent and preservative system. A 100 ml composition was prepared, having a final pH prior to storage of 8.2.

This method can readily be altered by the person skilled in the art to produce formulations having different component levels (e.g. other calcium or phosphate levels, or other sources of calcium or phosphate ions) or to use other ACP-stabilising agents (e.g. casein phosphopeptides, etc.).

OPN-10 refers to Lacprodan® OPN-10, available commercially from Arla Foods Ingredients (Arla Foods Ingredients Group P/S, Sønderhøj 10-12, 8260 Viby J, Denmark), which contains fractionated osteopontin from bovine milk.

The method involved preparing two intermediates; Intermediate A comprising a concentrated preservative system, and intermediate B comprising a flavour system.

TABLE 1

Intermediate A. 100x concentration of flavour/preservative solution.

| Ingredient | Product code | Quantity |
|---|---|---|
| Methyl paraben | H5501 | 1.00 g |
| phenoxyethanol | 77699 | 2.0 ml |
| Glycerol | G7893 | Make up to 10 ml |

TABLE 2

Intermediate B. Flavour system.

| Ingredient | Product code | Quantity |
|---|---|---|
| Base solution from Table 3 below. | | 10 g |
| Tego Betain | | 1.2 g |
| Flavour oil | | 0.5 g |

TABLE 3

Manufacture of finished product C

| Ingredient | Product code | Quantity |
|---|---|---|
| OPN-10 | | 3.0 g |
| Calcium chloride di-hydrate | S77016-269 | 2.87 g (of a 1M solution) |

TABLE 3-continued

Manufacture of finished product C

| Ingredient | Product code | Quantity |
|---|---|---|
| Monofluorophosphate | 344443 | 0.38 g |
| Di sodium hydrogen phosphate | S9390 | 16.0 ml of a 100 mM solution. |
| Tri sodium phosphate | S7778 | 16.0 ml of a 100 mM solution. |
| Preservative solution | From Intermediate A | 1.0 ml |
| Flavour system | From Intermediate B | 1.7 g |
| Xylitol | X3375 | 5.0 g |
| pH adjustment | 1M sodium hydroxide | 4.05 g |

1. To make the Intermediate A: Add 0.1 g of sodium methyl paraben to 0.7 g glycerol and mix in warm water bath to a clear solution. Add 0.2 g phenoxyethanol and mix until pale yellow clear solution. Make up to 10.0 ml with glycerol.
2. To make the finished product C: Add 40 g of deionised water to beaker and add 3.0 g of OPN-10 and rapidly mix until the solution clears. 3. Add 1M calcium chloride (0.1 ml/min) with rapid stirring.
4. Adjust the pH of the solution to 9.0 with 1M sodium hydroxide and maintain the pH at this value during the manufacturing procedure.
5. Add tri-sodium phosphate and di-sodium hydrogen phosphate (0.1 ml/min) to the OPN-10 solution.
6. Place Intermediate A preservative system into a warm water bath and pump into the OPN solution at 500 ul/min with rapid stirring. Result is a clear solution.
7. Add monoflurophosphate (MFP) solution made from dissolving MFP in 10 ml de-ionised water. Add slowly back to the OPN solution, pump rate 1.0 ml/min. Results in a very slightly cloudy pale yellow/white solution.
8. To make the Intermediate B: Take 10.0 ml of the OPN-10 solution and add to it to the tego betane and mix until clear.
9. Add 0.5 ml of flavour oil and mix until clear and then return Intermediate B back to the bulk.
10. Mix in xylitol.
11. Adjust the pH of the solution to 8.2 with 1M sodium hydroxide.
12. Make up to the final volume with deionised water.
13. Filter through a 0.22 um sterile filter.

This methodology has also been scaled up successfully to make a 2000 ml batch.

Example 2—Stability Testing of a 3% OPN-10 Formulation

In the present example, the chemical stability of formulations produced substantially according to Example 1 was assessed. Stability was assessed at ambient conditions (room temperature and humidity) and at accelerated conditions (40° C. and 75% relative humidity). Two formulations were prepared, one comprising 28.821 mM calcium and the other 19.2 mM calcium.
Formulations
MOC1, 3% OPN-10, 500 ppm fluoride as MFP, 28.821 mM Calcium.
MOC2, 3% OPN-10, 500 ppm fluoride as MFP, 19.2 mM Calcium.
Each batch, MOC1 and MOC2, was divided into six 75 ml batches. The batches had a baseline assay to record: Free and total fluoride, pH, absorbance at 400 nm and free calcium. Three of each of the batches were then placed into ambient storage (room temperature and humidity) in sealed glass bottles. The remaining three of each batch were placed into accelerated storage (40° C. and 75% relative humidity). The stability of the formulations was measured after 1, 2 and 3 months.

Measurement Parameters
The concentration of free fluoride. This is the fluoride ion concentration that is available in the formulation and will be available on application in the oral cavity. If fluoride and calcium ions could interact they would form an insoluble calcium fluoride molecule that would be non-efficacious in the oral cavity. The presence of free fluoride ions is an indication that calcium and fluoride ions are successfully "hidden" from each other when in the formulation.

Total fluoride. This is a measurement of the amount of fluoride that was added in the manufacture of the batch and confirmation that the concentration remains constant over the stability testing period.

pH is a measurement to indicate chemical or physical changes occurring in the formulation. It is also monitored to form a specification of the starting pH of future batches so that the final pH of the batch remains within specification.

Free calcium is a measurement of chemical stability, in that, if calcium and fluoride ions could interact they would form an insoluble calcium fluoride molecule that would be unifications in the oral cavity. The presence of free calcium is an indication that calcium and fluoride ions are successfully "hidden" from each other when in the formulation.

Absorbance is a measure of the clarity of the solution. An increase in absorbance is an indication of particulate matter and chemical instability.

Results
1 Month Stability
Free fluoride concentration: Ambient storage, the MOC1 formulation has free fluoride that is 17% of the total fluoride and MOC2 12.6% of total fluoride.
Accelerated storage, MOC1 68% of total fluoride, MOC2 49% of total fluoride.
There is a slight increase from the initial measurement in free fluoride for ambient stored batches and a large increase in free fluoride for accelerated batches.
For all batches the total fluoride is at 500 ppm.
The pH for both formulations gradually changed. The ambient stored samples the pH has declined by about 0.5 and accelerated storage by about 0.7.
Free calcium: MOC1 the free calcium has reduced by 0.4 mM in the ambient storage and 0.45 mM for the accelerated storage. MOC2 has reduced by about 0.35 mM for ambient and accelerated storage.
There is no significant change in absorbance levels for all batches.
2 Month Stability
Free fluoride: Ambient storage, MOC1 36% of total fluoride, MOC2 30% of total fluoride.
Accelerated storage, MOC1 84% of total fluoride, MOC2 72% of total fluoride.
For all batches the total fluoride is at 500 ppm.
The rate of change in pH for both formulations are reducing and the pH is levelling off at about 6.4.
Free calcium: the concentration of free calcium has not changed from the month 1 results and remains at about 0.05 mM for ambient storage samples and 0.01 mM for accelerated storage.

There is no significant change in absorbance levels for all batches.

3-Month Stability

Free fluoride: Ambient storage, MOC1 45% of total fluoride, MOC2 40% of total fluoride.

Accelerated storage, MOC1 85% of total fluoride, MOC2 85% of total fluoride.

For all batches the total fluoride is at 500 ppm.

The rate of change in pH for both formulations has levelled off with a final value of about 6.3.

Free calcium: the concentration of free calcium has not changed from the month 1 results and remains at about 0.05 mM for ambient storage samples and 0.01 mM for accelerated storage.

There is no significant change in absorbance levels for all batches.

Conclusion

At the initial time point, directly after manufacture, there is very low concentrations of free fluoride and high concentrations of free calcium. Over the three month stability time period, the concentration of free fluoride increases to a maximum of about 85% of the total fluoride. The concentration of free calcium reduces to a minimum of about 0.05%. This process is accompanied by a change in the pH of the solution that reduces by about 1 pH unit. The observation that the solutions remain clear throughout the stability study and that after three months almost all of the fluoride ions remain free in the formulation indicates that both fluoride and of calcium ions have been successfully excluded from each other to result in a stable formulation. By way of comparison, a sodium fluoride formulation prepared in the same manner was unstable and precipitated immediately it was made.

Measurement Methods

1) Method of Free and Total Fluoride Analysis Method.

A method for measuring fluoride from MFP materials was adapted from "Available fluoride in toothpaste used by Brazilian children". Braz. Dent. J. 2010 21(5):3096-400. The method was performed as follows:

Materials.

Fluoride analysis using a Cole Parmer 27902-19 fluoride ion selective electrode.

Fluoride standards were made up from Cole Parmer 1000 ppm F stock solution 27503-13.

Solution pH was determined using a Metler Toledo pH electrode inlab413 with a Hanna pH meter Masses were determined using a Acculab Satorius balance.

Di water was supplied on tap and is RO purified and deionised.

Making the Calibration Standards.

Make a 1000 ppm F solution by adding 7.6 g MFP to 1 L di water.

Dilute a sample 1:10 to get a 100 ppm solution. Serial dilute 1 in 10 to get 100, 10 and 1 ppm solutions.

Take 1 ml from each of the three dilutions and add 1 ml of a 2M HCL solution.

Incubate overnight at 37° C. to hydrolyse.

Next day add 2 ml of a 1M NaOH solution.

Take a 1 ml aliquot and mix with 1 ml of TSAB.

Measure.

Plot mV vs (log) 12.5, 1.25 and 0.125. (concentration divided by 8).

Measuring Samples.

Take 1 ml of the test solution and add 1 ml of 2M HCl. (pastes need to be mixed thoroughly and centrifuged).

Incubate overnight at 37° C. to hydrolyse.

Next day add 2 ml of a 1M NaOH solution.

Take a 1 ml aliquot and mix with 1 ml of TSAB.

Measure.

The corresponding fluoride concentration should be multiplied by 8 to get the final concentration.

2) Method of Free and Total Fluoride Analysis Method.

The method for measuring calcium ions in solution was performed as follows:

Materials.

Ca analysis thermos Scientific Orion 9700BNWP.

Calcium standards were made up from $1\times10^{-2}$, $1\times10^{-3}$ and $1\times10^{-4}$ M calcium chloride stock solution.

Di water was supplied on tap and is RO purified and deionised.

Making the Calibration Standards.

Make a $1\times10^{-2}$ M solution by adding 1.4702 g calcium di hydrate to deionized water and making up to 1 L.

Take a 1 ml aliquot and mix with 1 ml of ISA (ionic strength adjuster 0.2M KCl).

Measure.

Plot mV vs (log) $5\times10^{-3}$, $5\times10^{-4}$, and $5\times10^{-5}$

Measuring Samples.

Take 1 ml of the test solution and add 1 ml of ISA.

Mix.

Measure.

The corresponding calcium concentration should be multiplied by 2 to get the final concentration.

Example 3—Remineralisation

The following work was conducted to assess remineralisation potential of formulations comprising OPN-10 stabilised amorphous calcium phosphate complexes.

Assay for Hydroxyapatite Remineralisation

A weight of 1 g of HA powder was placed into a 25 ml conical flask and a 10 mm magnetic follower added. The powder was gently stirred while 20 ml of the remineralising solution was added at time zero. Samples were withdrawn at intervals by means of a 1 ml micropipette and discharged into numbered microcentrifuge Eppendorf tubes. The withdrawn samples were centrifuged at 16,000×g for 3 min to pellet the HA powder. An aliquot of 100 µl of the supernatant was withdrawn and diluted into a suitable volume of distilled water. For remineralising solutions containing 40 and 60 mM phosphate, the dilution factors were 101 and 151, respectively. A volume of 500 µl of the diluted sample was used to develop the phosphomolybdate colour in another Eppendorf tube. During colour development, the phosphopeptide precipitated on addition of the molybdate reagent and was removed by centrifuging at 16,000×g for 3 min. Approximately 1.5 ml of the supernatant was removed and transferred to a semi-micro cuvette for determination of the optical density at 750 nm.

Preparation of Formulations

Two OPN-10-based samples were selected for assessing remineralisation for scaling up to 100 ml. These were a 4% OPN-10 formulation, containing 112 mM calcium and 69 mM phosphate, and a 2% OPN-10 formulation containing 48 mM calcium and 32 mM phosphate. The pH was recorded throughout the procedure. The scaled-up samples were used in the development of the remineralisation assay and for testing by other parties.

4% OPN-10:

Weigh out 4 g of phosphopeptide in a 150 ml beaker and add a suitable size of magnetic follower. With rapid stirring, add 30 ml of 100 mM tri-sodium phosphate. Add 15 ml of water. Pump in 11.2 ml of 1-M calcium chloride using a peristaltic pump at a flow rate of approximately 300 µl min⁻¹. Direct the outflow from the pump to just above the magnetic follower to rapidly disperse the added calcium solution. The required volume of 1-M calcium solution is placed in a Sterilin sample tube with a conical base so that the entire volume can be removed by the pump. Pump in 0.5 ml of distilled water to wash out the pump tubing and then pump in the phosphate solution. This comprises 10 ml of 100 mM di-sodium hydrogen phosphate, 29 ml of 100 mM tri-sodium phosphate and 1.5 ml of 1-M sodium hydroxide, total volume 40.5 ml. After all the phosphate has been added at 300 µl min⁻¹, pump in 0.5 ml of distilled water to wash out the pump tubing and continue pumping until the tubing is cleared. Pump in 1 ml of the preservative solution and again continue with pumping until the tubing is empty. Finally add the balancing volume (1.3 ml) of distilled water.

2% OPN-10:

Weigh out 2 g of phosphopeptide in a 150 ml beaker and add a suitable size of magnetic follower. With rapid stirring, add 60.3 ml of water mixed with 4.8 ml of 1-M calcium chloride. Pump in a mixture of 16 ml 100 mM di-sodium hydrogen phosphate, 16 ml of 100 mM tri-sodium phosphate and 1.9 ml of 1-M sodium hydroxide using a peristaltic pump at a flow rate of approximately 300 µl min⁻¹. Direct the outflow from the pump to just above the magnetic follower to rapidly disperse the added calcium solution. Pump in 1 ml of the preservative stock solution and record the final pH.

Remineralisation Assay

The objective here was to find out whether the selected formulations would transfer their calcium and phosphate to crystalline hydroxyapatite and if possible to measure the rate and extent of the transfer by measuring the concentration of phosphate in the supernatant as a function of time under the given assay conditions. Preliminary trials with MKnano HA powder showed that it was peptised by the phosphopeptides and was difficult to filter off or centrifuge down. The nanoXim powder was used instead and because of its larger particle size could be easily pelleted by centrifugation. One further refinement was required to the procedure. It was found that the phosphomolybdate reagent used to determine phosphate concentrations colourimetrically formed an insoluble complex with the phosphopeptides and had to be removed by centrifugation. With this additional step, accurate phosphate determinations were achieved. In control experiments, it was shown that the HA powder was effectively insoluble in water and so did not contribute to the phosphate supernatant concentration.

Figure 2:
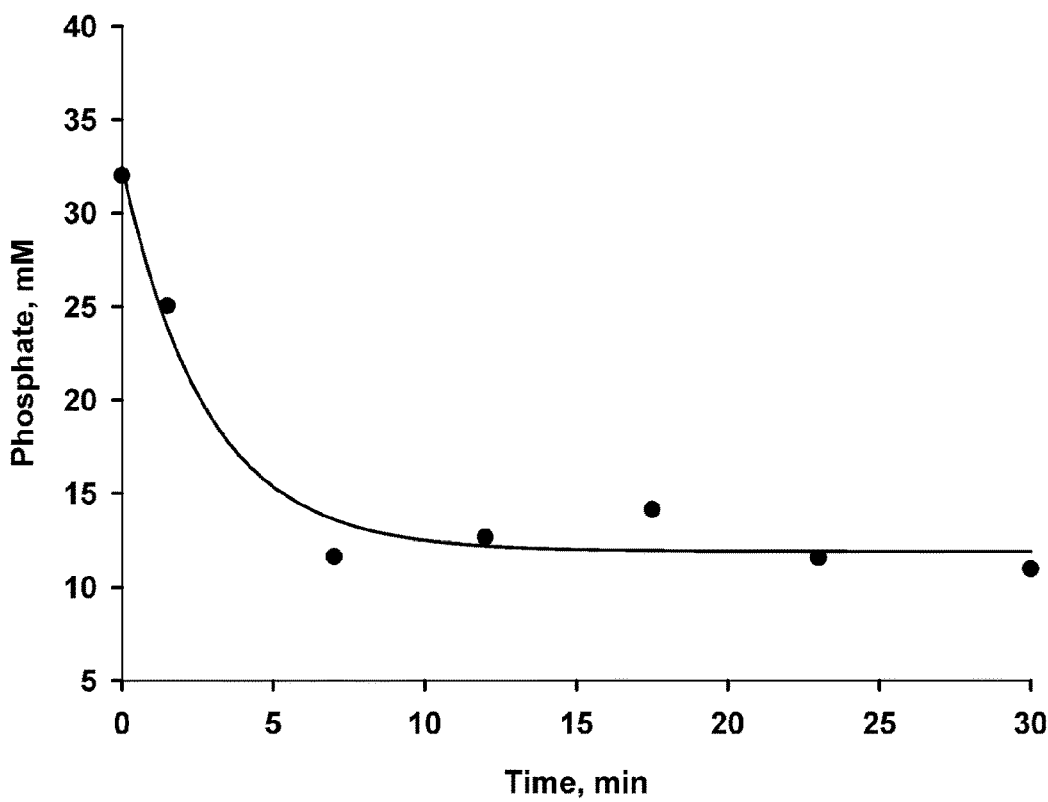
FIG. 2—Mineralisation of HA powder by a 2% OPN-10 formulation containing 32 mM phosphate.

FIGS. 1 and 2 shows the variation of supernatant phosphate concentration in the two formulations as a function of time. The solid line through the data points is from a simple model of the physical processes of mineral growth at high energy sites on the surface of the HA crystals in competition with the binding of the phosphopeptides at these same sites. FIG. 1 shows results of mineralisation of HA powder by a 4% OPN-10 formulation containing 69 mM phosphate, and FIG. 2 shows a 2% OPN-10 formulation containing 32 mM phosphate.

The formulation data are reasonably well fitted by an equation of the form $$[P_i]_t = [P_i]_{t=\infty} + \Delta[P_i] \cdot \exp(-t/\tau)$$

$$\Delta[P_i] = [P_i]_{t=0} - [P_i]_{t=\infty} \quad (1)$$

where $[P_i]_t$, $[P_i]_{t=\infty}$ and $[P_i]_{t=0}$ are the supernatant phosphate concentrations at time t, at equilibrium and at the start, respectively, $\Delta[P_i]$ is the concentration of phosphate transferred from the formulation to the HA powder and $\tau$ is the relaxation time for the rate of mineral growth. Another useful way of expressing the result is in the fractional increase in weight of mineral in the HA powder at equilibrium. One advantage of this measure is that it may be less dependent on the specific details of the assay such as the weight of powder and volume of formulation. However, it does require an assumption of which phase of calcium phosphate grows on the HA powder. The most reasonable assumption is that the HA powder nucleates further HA. Thus, assuming that the growth is entirely in the form of HA, formula mass M, containing v atoms of phosphorus per formula and that w g of HA powder are suspended in V litres of formulation, the fractional increase in mass (Δ w/w) is given by $$\frac{\Delta w}{w} = \Delta[P_i] \frac{VM}{wv} \quad (2)$$

Parameters derived from fitting the experimental data to equation (1) and the derived value from equation (2) are provided in Table 4.

TABLE 4

Fitted parameters for the rate and extent of HA powder mineralisation by the formulations

| Formulation | $[P_i]_{t=0}$ mM | $[P_i]_{t=\infty}$ mM | $\Delta[P_i]$ mM | Δw/w % | τ min |
|---|---|---|---|---|---|
| 2% OPN-10 | 32.0 | 11.9 | 20.1 | 6.7 | ~2.8 |
| 4% OPN-10 | 69.0 | 42.6 | 26.4 | 8.8 | 12.0 |

The rates of growth of the mineral in the 2% OPN-10 formulation was too fast to measure with any degree of precision. Essentially the transfer of mineral from the formulation to the HA powder was complete within a few minutes of contact (τ~2 min). Compared to the 2% formulation, the 4% OPN-10 formulation worked more slowly (τ~12 minutes) but transferred a similar quantity of phosphate to the HA at equilibrium. Further optimisation of the formulations should lead to even better results.

Figure 3:
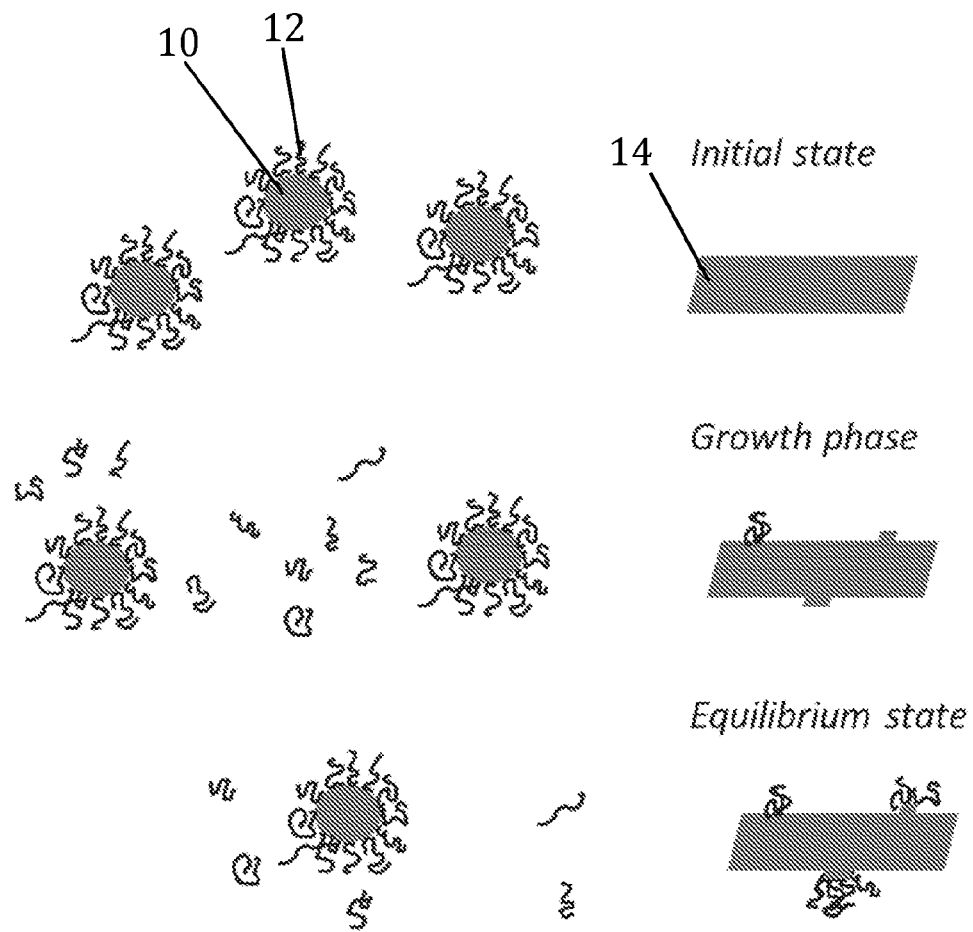
FIG. 3.—Diagram of HA crystal growth at high energy growth sites. Growth of the HA crystals is at the expense of particles of sequestered amorphous calcium phosphate. Sequestering phosphopeptides are released as the ACP dissolves. The free peptides bind to the growth sites preventing or slowing crystal growth and eventually an equilibrium state is reached in which no further growth of the HA occurs.
Figure 4:
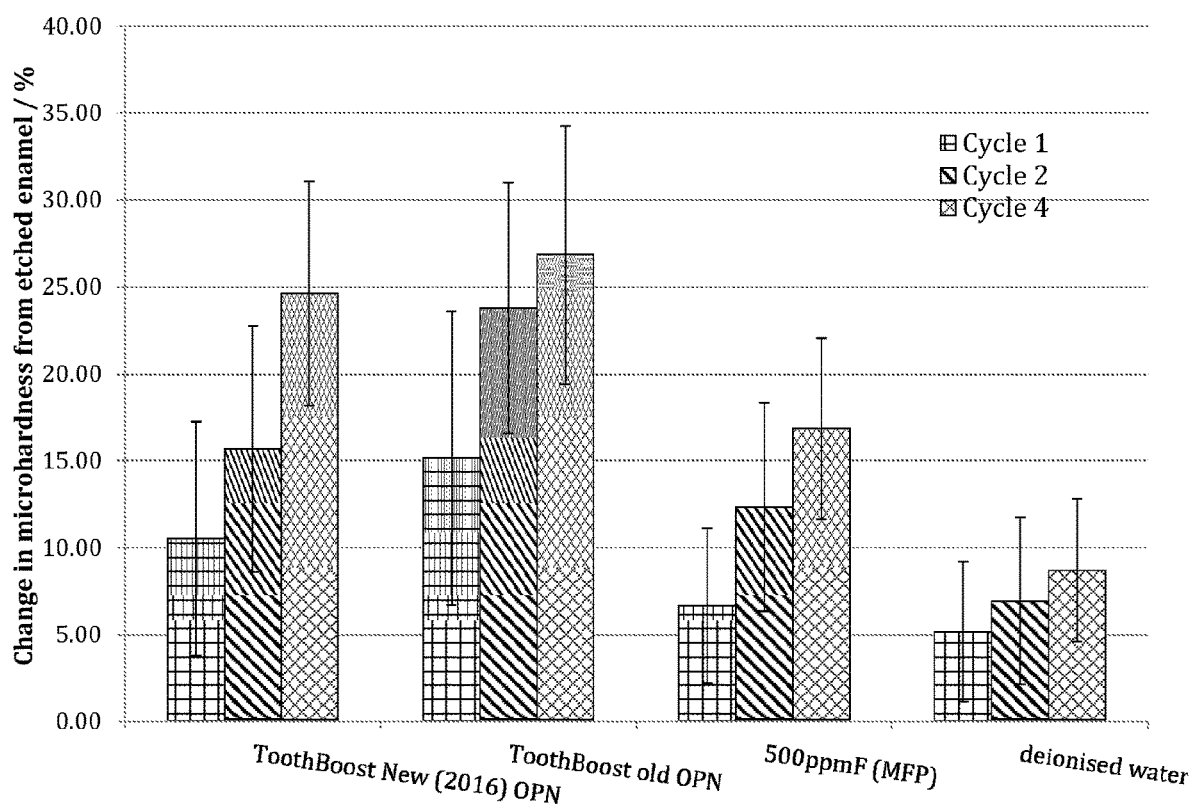
FIG. 4—Vickers Microindentation re-hardening study for ToothBoost (the term "ToothBoost" is used herein at some points to describe formulations according to the present invention) new and old OPN-10 batches, 500 ppmF (MFP) and deionised water. The graph shows the change in Vickers microindentation hardness values after treatment on days 1, 2 and 4. Error bars are SD. N=10 human enamel per treatment.

Not all the phosphate was transferred to the mineral and in the model, a diagram of which is shown in FIG. 3, this can be explained by the generation of free phosphopeptides 12 as the sequestered amorphous calcium phosphate 10 dissolves and is incorporated in the HA crystals 14. The liberated phosphopeptides are then able to bind to the high-energy sites on the HA crystals and block further growth.

Conclusions

The samples used in these experiments demonstrated mineralisation of a hydroxyapatite powder. The 2% sample, in particular, was able to mineralise the HA powder within a very short time, thus indicating good potential for use in rapidly effective spray formulations.

Example 4—Microindentation Study, OPN-10 Containing Formulations

1. Objectives

Citric acid eroded human enamel specimens were placed into a cycling re-mineralisation model where they were cycled between a treatment, artificial saliva and citric acid five times a day over five days. Three different treatments were tested and were: 1. 2% OPN formulation containing 500 ppm fluoride. 2. 500 ppm fluoride solution. 3. Deionised water. At the end of each of the five days the micro hardness of the enamel was measured by Vickers microindentation to determine the extent of the re-mineralisation of the enamel lesions.

2. Method

The microhardness of the enamel was determined by indentation using a Vickers diamond-tip indenter. Each hardness value was determined from the average of ten individual measurements made centrally on each enamel specimen using 1.9N force over an indent time of 20 seconds. At the start of each set of measurements a calibration check was performed using a standard metal block to ensure the reproducibility of microhardness was within 3% of the test block micro hardness.

The three treatment groups of six enamel specimens were placed into a dedicated water bath and the treatment procedure was as follows:

- Solutions were pre-incubated to 37° C. before use and incubations performed at 37° C.
- The enamel specimens were immersed in 50 ml of one of the assigned test solutions and timed for two minutes.
- The test solution aspirated and 100 ml artificial saliva was then added and timed for thirty minutes.
- The artificial saliva was aspirated and 100 ml of 1% citric acid, pH 3.75 solution added and timed for one minute, solution was at room temperature.
- The citric acid solution was aspirated and the enamel discs rinsed with DI water.
- The cycling procedure was repeated a total of five times.
- After the five treatments, the enamel specimens were rinsed allowed to dry and the microhardness measured.
- The enamel was then placed back into the artificial saliva and incubated at 37° C. overnight.
- The process was repeated for five days.

3. Results

The result of the microindentation cycling study shows that all three formulations; OPN, sodium fluoride solution and DI water gave an increase in the hardness of the eroded enamel, to differing degrees, over the five-day study. The OPN and sodium fluoride solutions were statistically superior to deionised water at all time points. The OPN solution gave a progressively greater remineralisation effect compared to the sodium fluoride solution and by day five was statistically superior to sodium fluoride. Overall the trend in remineralisation followed the scheme:

| | |
|---|---|
| OPN = NaF > DI water | Day 1 |
| OPN = NaF > DI water | Day 2 |
| NaF = OPN > DI water | Day 3 |
| OPN = NaF > DI water | Day 4 (probability 0.06) |
| OPN > NaF > DI water | Day 5 |

Example 5—Formulation and Manufacture Procedure for 3% OPN-10 Base for Flavour Tasting ML778, 100 ml with Soft Mint (Final pH 8.2.)

Described below is a further manufacturing procedure for a composition according to the present invention, the composition comprising 3% OPN-10 (w/w) with a soft mint flavouring agent and a preservative system. A 100 ml composition was prepared, having a final pH prior to storage of 8.2.

As above, OPN-10 refers to Lacprodan® OPN-10, available commercially from Arla Foods Ingredients (Arla Foods Ingredients Group P/S, Sønderhøj 10-12, 8260 Viby J, Denmark), which contains fractionated osteopontin from bovine milk.

The method involved preparing two intermediates; Intermediate A comprising a concentrated preservative system, and intermediate B comprising a flavour system.

TABLE 5

Intermediate A. Preservative solution.

| Ingredient | Product code | Quantity |
|---|---|---|
| Methyl paraben | 85265 | 1.00 g |
| phenoxyethanol | 77699 | 2.0 ml |
| Glycerol | G7893 | Make up to 10 ml |

TABLE 6

Intermediate B. Flavour system.

| Ingredient | Product code | Quantity |
|---|---|---|
| Base solution from C below. | | 10 g |
| Tego Betain | | 1.2 g |
| Flavour oil | | 0.3 g |
| saccharine | | 0.08 |

TABLE 7

C. Manufacture of finished product

| Ingredient | Product code | Quantity |
|---|---|---|
| OPN-10 | B490239 | 3 g |
| Calcium chloride di-hydrate | S77016-269 | 2.87 g (of a 1M soln) |
| Monoflurophosphate | 344443 | 0.38 |
| Di sodium hydrogen phosphate | S9390 | 16 ml |
| Tri sodium phosphate | S7778 | 16 ml |
| Preservative solution | From Intermediate A | 1 ml |
| Flavour system | From Intermediate B | 1.58 g |
| Xylitol | X3375 | 5.0 g |
| pH adjustment | 1M sodium hydroxide | |

Procedure:

1. To make the Intermediate A: Add 1.0 g of sodium methyl paraben to 7.0 g glycerol and mix in warm water bath to a clear solution. Add 2.0 g phenoxyethanol and mix until pale yellow clear solution. Make up to 10.0 ml with glycerol.
2. To make the finished product C: Add 50 g of deionised water to beaker and add 3.0 g of OPN-10 and rapidly mix until the solution clears.
3. Add monoflurophosphate (MFP) solution made from dissolving MFP in 10 ml de-ionised water. Add slowly back to the OPN solution, pump rate 5.0 ml/min. Results in a very slightly cloudy pale yellow/white solution.
4. Add 1M calcium chloride (0.1 ml/min) with rapid stirring.
5. Adjust the pH of the solution to 9.0 with 1M sodium hydroxide and maintain the pH at this value during the manufacturing procedure.
6. Add tri-sodium phosphate and di-sodium hydrogen phosphate (0.1 ml/min) to the OPN-10 solution.
7. Place Intermediate A preservative system into a warm water bath and pump into the OPN solution at 500 µl/min with rapid stirring. Result is a clear solution.
8. To make the Intermediate B: Take 10.0 ml of the OPN-10 solution and add to it 1.2 g tego betane and saccharine and mix until clear.

9. Add flavour oil and mix until clear and then return Intermediate B back to the bulk.
10. Mix in 5 g xylitol.
11. Adjust the pH of the solution to 8.2 with 1M sodium hydroxide.
12. Make up to 100 ml with deionised water.
13. After 24 hr Filter through a 0.22 μm sterile filter.

Example 6—Further Remineralisation Studies

A four-day cycling treatment microindentation model to further assess the remineralisation potential for a formulation produced according to the following procedure (referred to as MOF).

TABLE 8

Intermediate A: 100x concentration of preservative solution

| Ingredient | Quantity |
|---|---|
| Methyl paraben | 1.00 g |
| phenoxyethanol | 2.0 g |
| Glycerol | Make up to 10.0 g |

TABLE 10

Intermediate B: Flavour system

| Ingredient | Quantity |
|---|---|
| Base solution from Table 3 | 9.5 g |
| Tego Betain | 1.2 g |
| Flavour oil | 0.5 g |
| saccharine | 0.08 g |

TABLE 10

Manufacture of finished product C.

| Ingredient | Product code | Quantity |
|---|---|---|
| OPN-10 | B490239 | 3 g |
| Calcium chloride di-hydrate | S77016-269 | 2.87 g (of a 1M solution) |
| Monoflurophosphate | 344443 | 0.38 g |
| Di sodium hydrogen phosphate | S9390 | 16.0 g (of a 0.1M solution) |
| Tri sodium phosphate | S7778 | 16.0 g (of a 0.1M solution) |
| Deionised water | | 50.0 g |
| Preservative solution | From Intermediate A | 1.0 g |
| Flavour system | From Intermediate B | 1.78 g |
| Xylitol | X3375 | 5.0 g |
| pH adjustment | 1M sodium hydroxide | |

Procedure:
Procedure.
1. To make the Intermediate A: Add 1.0 g of sodium methyl paraben to 7.0 g glycerol and mix in warm water bath to a clear solution. Add 2.0 g phenoxyethanol and mix until pale yellow clear solution. Make up to 10.0 g with glycerol.
2. To make the finished product C: Add 40 g of deionised water to beaker and add 3.0 g of OPN-10 and rapidly mix until the solution clears.
3. Add monoflurophosphate (MFP) solution made from dissolving MFP in 10.0 g de-ionised water. Add slowly back to the OPN solution, pump rate 5.0 ml/min. Results in a very slightly cloudy pale yellow/white solution.
4. Add 1M calcium chloride (0.1 ml/min) with rapid stirring.
5. Adjust the pH of the solution to 9.0 with 1M sodium hydroxide and maintain the pH at this value during the manufacturing procedure.
6. Add tri-sodium phosphate and di-sodium hydrogen phosphate (0.1 ml/min) to the OPN-10 solution.
7. Place Intermediate A preservative system into a warm water bath and pump into the OPN solution at 500 ul/min with rapid stirring. Result is a clear solution.
8. To make the Intermediate B: Take 9.50 g of the OPN-10 solution and add to it 1.2 g tego betane and 0.08 g saccharine and mix until clear.
9. Add 0.50 g flavour oil and mix until clear and then return Intermediate B back to the bulk.
10. Mix in 5 g xylitol.
11. Adjust the pH of the solution to 8.2 with 1M sodium hydroxide.
12. Make up to 100 g with deionised water.
13. After 24H Filter through a 0.22 μm sterile filter.

Human enamel lesions were treated five times a day for four days with either a MOF formulation with a new batch of OPN-10 (ToothBoost New (2016) OPN), a MOF formulation with an older batch of OPN-10 (ToothBoost Old OPN), a 500 ppm fluoride solution (produced from monofluorophosphate) or deionised water.

The formulations were applied to the enamel lesions using a spray pump with the intention to align the study with prospective in vivo product use. A single actuation of the spray pump delivers approximately 0.15 g of product. The treatment procedure is as follows:

The enamel specimens were placed into artificial saliva at 37° C. for 1 hour before the start of the study.

The enamel specimens were removed from the artificial saliva and gently blotted with tissue paper to remove excess moisture.

The four groups were then selected and placed into a dedicated container, one for each group.

Each enamel specimen was then sprayed with approximately 0.15 g of either MOF new OPN-10, MOF old OPN-10, 500 ppm fluoride solution or deionised water.

The enamel was then returned to the artificial saliva and incubated at 37° C. for 1 hour.

The treatment process was repeated a total of five time in a day.

At the end of the day the enamel was rested in artificial saliva at room temperature.

The treatment process was repeated a total of four days.

After days one, two and four the microhardness of the enamel was measured by microindentation.

The intention of the study was to: 1. Determine if the new OPN-10 raw material performs as well as the old OPN-10 raw material. Rank the ability of the formulations to remineralise erosive lesions after sequential application over four days.

TABLE 11

The key ingredients for each of the formulations. 1500 U/L phosphatase was used in the artificial saliva for this study.

ML792

| | |
|---|---|
| ToothBoost MOF using OPN-10 manufactured in 2016. (BN G090239) | 3% OPN-10, Tri-sodium and di-sodium phosphate, calcium chloride, flavour system, preservatives, xylitol, 500 ppmF as MFP. |
| ToothBoost MOF using OPN-10 manufactured before 2014. | 3% OPN-10, Tri-sodium and di-sodium phosphate, calcium chloride, flavour |

TABLE 11-continued

The key ingredients for each of the formulations. 1500 U/L phosphatase was used in the artificial saliva for this study.

| ML792 | |
| --- | --- |
| (BN B490239) | system, preservatives, xylitol, 500 ppmF as MFP. |
| 500 ppm fluoride from MFP | 500 ppm fluoride from MFP |
| Deionised water | Deionised water |

Note -
(Phosphatase enzyme is in abundance in saliva and it cleaves off the fluoride from the phosphate from the monofluorophosphate, and so releases the free fluoride which is then biologically active. This is a standard procedure when using MFP dentifrice formulations in in vitro testing. 1500 Units of phosphatase can hydrolyse one Litre of a 1400 ppm solution of MFP in four minutes at 37° C., 15 minutes at room temperature).

In summary:

1. A comparison of the OPN-10 and freshly prepared OPB-10 batches indicates that (statistically significant after 2 treatment cycles) the old OPN-10 remineralise more effectively than the new OPN-10 batches. This is because the product requires a period of days after manufacture to reach its optimal efficacy because of the molecular re-arrangement taking place.

2. After 4 treatment cycles, the old and new OPN batches are statistically the same indicating the dose response eventually surpasses any effects that may be seen due to time after manufacture. Both OPN formulations are statistically superior to 500 ppmF from MFP alone. All formulations are statistically superior to deionised water.

TABLE 12

The change in microhardness values as a percentage increase from the acid eroded enamel lesions. SD is standard deviation.

| | Cycle 1 | SD | Cycle 2 | SD | Cycle 4 | SD |
| --- | --- | --- | --- | --- | --- | --- |
| ToothBoost New (2016) OPN-10 | 10.53 | 6.72 | 15.68 | 7.07 | 24.62 | 6.48 |
| ToothBoost Old (pre 2014) OPN-10 | 15.14 | 8.44 | 23.80 | 7.21 | 26.85 | 7.41 |
| 500 ppmF (MFP) | 6.66 | 4.46 | 12.33 | 5.97 | 16.85 | 5.22 |
| deionised water | 5.15 | 4.03 | 6.93 | 4.81 | 8.70 | 4.10 |

Example 7—Remineralisation Analysis by Microindentation and Calcivis Studies 1 Introduction A collaborative study was setup to measure the remineralisation of erosive lesions in bovine enamel after treatment five times a day for seven days. The intention of the study was to 1.

Assess the viability of using Calcivis Ltd's enzyme linked calcium luminescence technology to measure calcium concentrations in the intra micro pores of enamel during de-mineralisation under erosive conditions and the subsequent remineralisation. 2. To compare the results of the Calcivis's enzyme linked calcium luminescence results to microindentation studies.

Microindentation is a recognised method for the measurement of the hardness of materials and is defined by ASTM E384 (American Section of the International Association for Testing Materials). A diamond tipped four-sided pyramid indenter is pressed into the surface of the test material using a defined force. The dimensions of the resulting indent is then measured using a microscope and a mathematical manipulation of the dimensions results in a hardness value. There is a direct correlation between the hardness of enamel and the degree of mineralisation and so microindentation has found significant use for the measurement of enamel de- and re-mineralisation.

The Calcivis Imaging System is a method to measure free calcium ions from within the fluid filled pores of dental enamel. In cases where caries lesions are present, or where acid erosion has taken place, free calcium ion concentration is increased within the pores. This increase in concentration provides a marker for the Calcivis Imaging System to detect active de-mineralisation associated with caries activity and enamel erosion.

Three test formulations were manufactured: Toothboost, 500 ppm fluoride solution made from monoflurophosphate, and deionised water. Bovine enamel specimens were treated and the resulting microhardness during the treatment procedure measured. At appropriate time points during the procedure the enamel specimens were sent to Calcivis for luminescence analysis. The identities of the enamel treatments were not disclosed to Calcivis until after the study had completed.

2 Materials and Methods

Microindenter: Buehler micromet 5104 UKAS calibration certification #DIR1418 with certified Vickers diamond.
Polishing machine: Buehler Automet/Ecomet 250.
pH meter: Hanna 213.
Deionised water from the laboratory on tap RO supply.
Spray packs for dispensing the test formulations: 1033821A1 supplied by Dentherapy 13 Feb. 2017.
Phosphatase from Sigma P0114
Calcivis benchtop imaging equipment consist of:
  containing box to eliminate all external light
  camera
  laptop with Pylon software to control camera
  light source
  photo protein source (multistep syringe and nozzle)

TABLE 13

Artificial saliva made from:

| | |
| --- | --- |
| Magnesium Chloride | 0.2 mM |
| Calcium chloride di-hydrate | 1.0 mM |
| Potassium di-hydrogen orthophosphate | 4.0 mM |
| HEPES (N-2Hydroxyethylpiperazine-N'-ethanethesulphonic acid) | 20 mM |
| Potassium chloride | 16.0 mM |
| Ammonium chloride | 4.5 mM |
| pH adjusted to 7.0 with sodium hydroxide. | |
| Phosphatase | 1500 U/L |

TABLE 14

Formulations used:

| Formulation | Formulation reference |
| --- | --- |
| 500 ppm fluoride solution (MFP). | 3.8 g MFP in 1000 ml deionised water |
| Toothboost. | See below for details |
| Deionised water | From lab supply |

The test formulations were dispensed into a spray pack for the application to the enamel samples and stored at 37° C. Artificial saliva with 1500 U/L phosphatase was stored at 37° C. (Note—1500 Units of phosphatase can hydrolyse one Litre of a 1400 ppm solution of MFP in four minutes at 37° C., 15 minutes at room temperature).

3 Methods 3.1 Specimen Preparation 10 mm diameter enamel cores were trepanned from the facial side of bovine incisors and mounted in 25 mm diameter resin discs. The underside of the disc was flattened using p60 grit paper and the enamel side ground with p600 paper to expose the enamel and the surface polished using 1200 and then 2500 grit paper and finally 1 um diamond polish to reveal a highly-polished enamel surface. The discs were then rinsed under deionised water and sonicated for five minutes and stored at 5° C. in a humid environment until required.

3.2 Formation of Erosive Lesions

Erosive lesions were formed in the enamel specimens by incubating the enamel resin disc in a 1% solution of citric acid monohydrate, pH adjusted to 3.75, for ten minutes at 37° C. The enamel discs were then rinsed in deionised water and sonicated for five minutes.

3.3 Microindentation Method

The microhardness measurements of the enamel was made using a Vickers diamond-tip indenter. Each hardness value was determined from the average of ten individual measurements made centrally on each specimen using 0.2N force over an indent time of 20 seconds. The indent size was measured using ×50 magnification which was then converted to microhardness values.

3.4 Calcivis Imaging Method

Assessment was made by imaging the samples as a monochrome image under visible lighting, followed by a luminescent image obtained by applying 50 µL of freshly reconstituted CALCIVIS photoprotein to the enamel surface in the dark. Any luminescent signal detected by the sensor is therefore a result of the reaction between the photoprotein and free calcium ions on the enamel surface. Fuji (Imagej) software was used to convert the luminescent intensity to a colour coded scale (Royal).

The enamel discs were rinsed with water and dried with air. A ring of dental wax was placed around the exposed enamel, creating a well to ensure complete coverage with the photoprotein.

The Calcivis photoprotein was reconstituted and loaded into a multistep syringe. The system tubing was primed to remove any bubbles.

The camera exposure time was set to 2000 ms and set to take continuous images. The light source was turned on. The enamel disc was placed under the camera and the focus and light adjusted to give a clear image of the disc. A single visible light image frame was captured and saved.

The camera exposure time was set to 2000000 ms and setup for single image capture and the light source was turned off. Image capture was started and immediately after (within 0.5 s) 100 µl Calcivis photoprotein was applied to the enamel surface. The luminescent image was saved.

To improve visualisation of the luminescent images the 'Royal' look-up table was applied. This gives a false colour image with low intensity signal displayed as blues and higher intensity as yellows.

To allow quantitative analysis of the samples the mean pixel intensity of a 100px radius circle in the centre of the image was measured.

4.0 Treatment Procedure

An initial microindentation measurement of the sound (non-treated) enamel was first made to ensure the enamel is sufficiently mineralised for the purpose of this study, microhardness acceptance criteria is >350 VHN. The enamel discs were then posted to Calcivis. On return, the enamel discs were then acid etched with 1% w/w solution of citric acid, as indicated in 3.2 above. The microhardness measurements of the erosive lesions were then made and the hardness values used to group the enamel specimens into three groups of ten so that each group has a similar range of hardness values. The enamel specimens were then posted to Calcivis for luminescence measurements and on their return the following treatments were made.

The enamel then proceeds with the following treatment cycles.

The Enamel is placed into artificial saliva for 1 hour before the start of the study.

The enamel is removed from the artificial saliva and gently blotted with tissue paper to remove excess moisture.

Each enamel specimen is then sprayed with approximately 0.15 g of treatment formulation (either Toothboost, 500 ppm fluoride (MPF) solution, or deionised water depending on group).

The enamel is then returned to the artificial saliva and incubated at 37° C. for 1 hour.

The process is repeated five for a total of times in a day.

At the end of the day the enamel is rested in artificial saliva at room temperature.

The treatment is repeated a total of seven days.

After day seven the enamel specimens are measured by microindentation and send to Calcivis for the calcium assay.

5.0 Results 5.1 Microindentation Results

Figure 5:
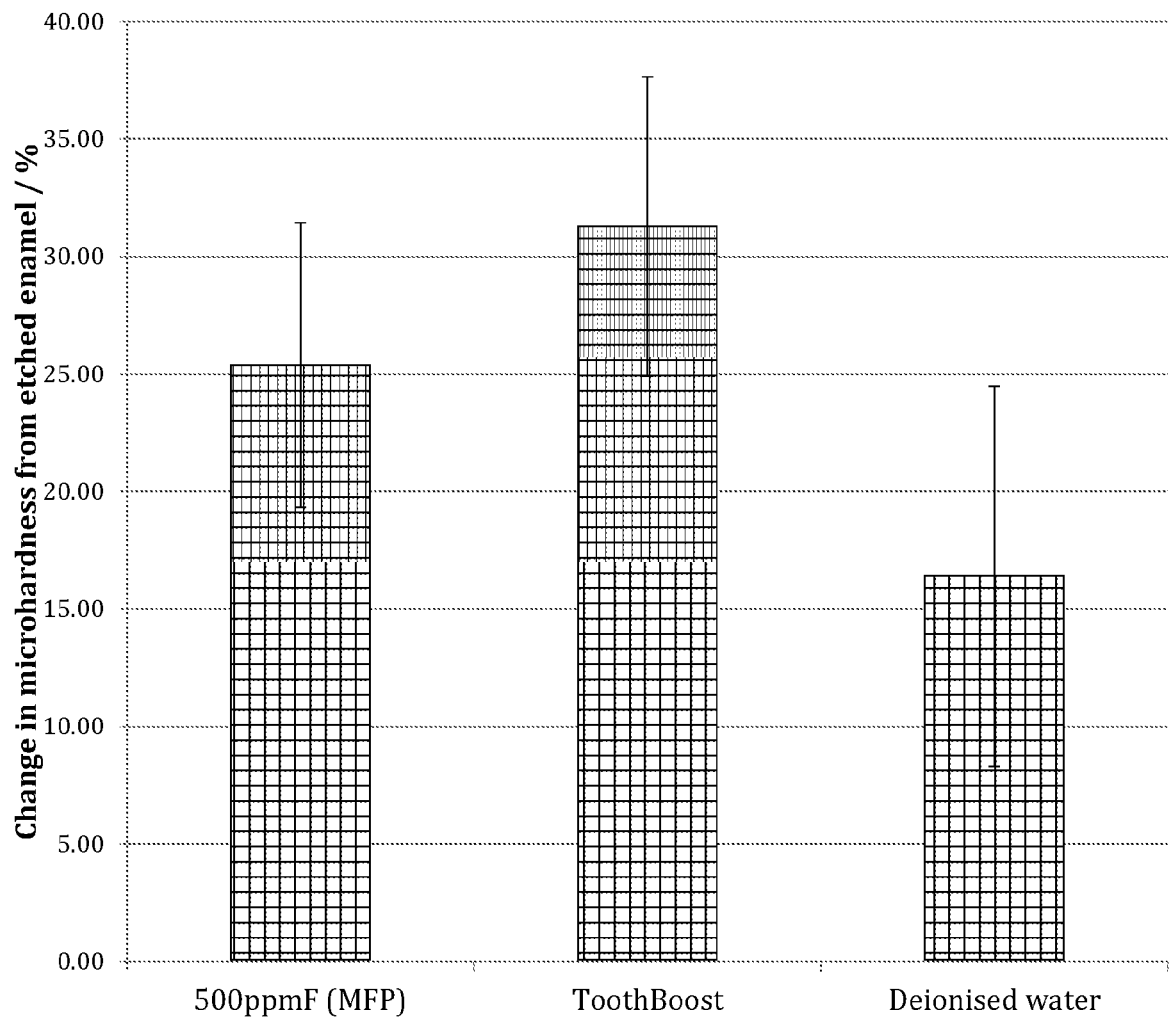
FIG. 5—The change in microhardness of the erosive lesions after treatment for seven days. Vickers Microindentation re-hardening of citric acid erosive lesions in human enamel treated with either 500 ppm fluoride (MFP), Toothboost or deionised water after seven days. N=10 human enamel. Error bars are SD.

The change in microhardness was calculated as a percent of the baseline value. These values are shown in table 15 and FIG. 5.

TABLE 15

The change in microhardness of the remineralised enamel lesions as a percent of the enamel lesions.

| Treatment formulation | Change in enamel hardness from eroded enamel/% | SD |
|---|---|---|
| 500 ppmF (MFP) | 25.39 | 6.05 |
| ToothBoost | 31.28 | 6.37 |
| Deionised water | 16.40 | 8.08 |

5.2 Calcivis Luminescence Results

Figure 6:
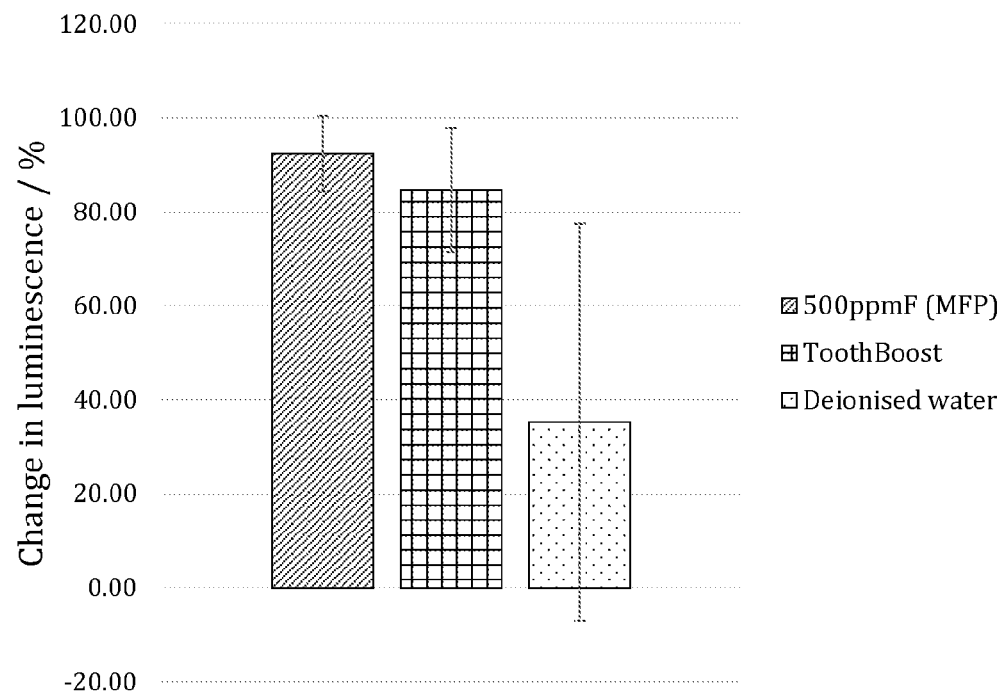
FIG. 6—The change in luminescence of the erosive lesions after treatment for seven days. The change in luminescence of citric acid erosive lesions after treatment with either 500 ppm fluoride (MFP), Toothboost or deionised water after seven days. N=10 human enamel. Error bars are SD.

The change in luminescence at each time point was calculated as a percent change from the baseline value. These values are shown in table 16 and FIG. 6.

TABLE 16

The change in luminescence of the remineralised enamel lesions as a percent of the enamel lesions.

| Treatment formulation | Change in enamel luminescence from eroded enamel/% | SD |
|---|---|---|
| 500 ppmF (MFP) | 92.44 | 8.00 |
| ToothBoost | 84.66 | 13.17 |
| Deionised water | 35.22 | 42.29 |

Figure 7:
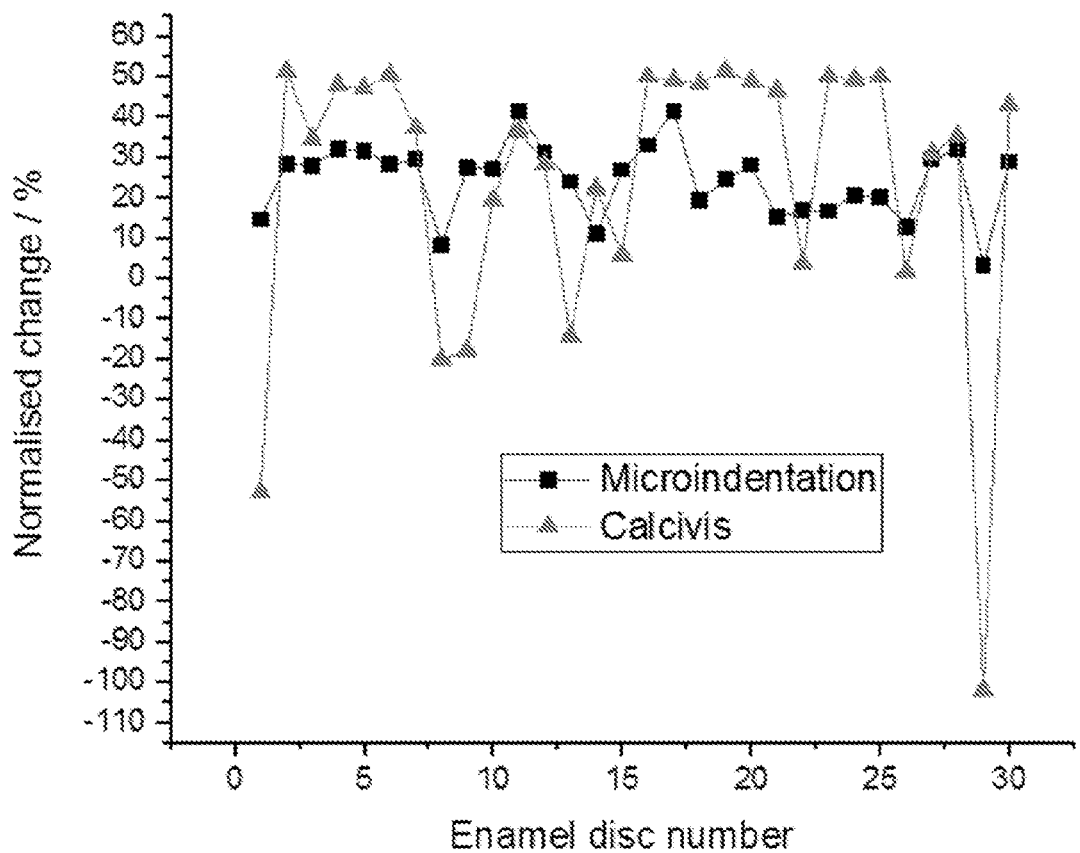
FIG. 7—Graph showing a comparison between the changes in microhardness and luminescence of bovine enamel discs, normalized to the difference in averages between the two groups.

A comparison of the individual measurements made for each of the enamel discs was made to identify similarities between the two measurement methods. The Calcivis luminescence data was normalised so that the scale fell within that of the microindentation data. This was done by subtracting the difference between the mean microindentation result and the mean luminescence result. The values are shown in Table 17 and FIG. 7.

TABLE 17

The calculation of the normalised luminescence values.

| Disc number | indentation value | | Luminescence value | Normalised luminescence |
|---|---|---|---|---|
| 1 | 14.56002 | | −6.61 | −53.03 |
| 2 | 28.38239 | | 97.70 | 51.28 |
| 3 | 27.92691 | | 80.99 | 34.58 |
| 4 | 31.96067 | | 94.29 | 47.87 |
| 5 | 31.64767 | | 93.38 | 46.96 |
| 6 | 28.28084 | | 96.84 | 50.42 |
| 7 | 29.55862 | | 83.58 | 37.17 |
| 8 | 8.192099 | | 26.39 | −20.03 |
| 9 | 27.35848 | | 28.46 | −17.95 |
| 10 | 27.07733 | | 65.85 | 19.44 |
| 11 | 41.36693 | | 82.98 | 36.56 |
| 12 | 31.35942 | | 74.55 | 28.13 |
| 13 | 24.01148 | | 32.18 | −14.24 |
| 14 | 10.90307 | | 68.70 | 22.28 |
| 15 | 26.85711 | | 52.25 | 5.84 |
| 16 | 33.03047 | | 96.30 | 49.88 |
| 17 | 41.35167 | | 95.45 | 49.04 |
| 18 | 19.27738 | | 94.59 | 48.18 |
| 19 | 24.43248 | | 97.81 | 51.39 |
| 20 | 28.07899 | | 95.24 | 48.82 |
| 21 | 15.25428 | | 92.80 | 46.39 |
| 22 | 16.65392 | | 50.00 | 3.59 |
| 23 | 16.61641 | | 96.38 | 49.96 |
| 24 | 20.51332 | | 95.80 | 49.38 |
| 25 | 19.91233 | | 96.32 | 49.90 |
| 26 | 12.7531 | | 48.17 | 1.75 |
| 27 | 29.3997 | | 77.27 | 30.86 |
| 28 | 31.84539 | | 81.62 | 35.21 |
| 29 | 3.236051 | | −55.56 | −101.97 |
| 30 | 28.90084 | | 89.42 | 43.01 |
| Mean indentation | 24.35665 | Mean luminescence | 70.77084 | |

6.0 Statistical Evaluation

A statistical evaluation of the change in microhardness and the change in luminescence after treatment and re-mineralisation after seven days was performed using one way ANOVA and Tukey means comparison. Data sets were first tested for normal distribution using Shapiro-Wilks normality test. All data sets had a probability factor greater than 0.05 indicating they were normally distributed. Table 18 shows the results of the microindentation data and Table 19 the results of the luminescence data.

TABLE 18

Pair wise comparison of the paste formulations show that when Sig = 1 the means difference is significant at the 0.05 level.

| | MeanDiff | SEM | q Value | Prob | Sig | LCL | UCL |
|---|---|---|---|---|---|---|---|
| MFP-Toothboost | 5.89 | 2.78 | 3.00 | 0.05 | 1 | 0.06 | 11.73 |
| MFP-Water | −8.99 | 3.19 | 3.98 | 0.01 | 1 | −15.69 | −2.28 |
| Toothboost-Water | 14.88 | 3.25 | 6.47 | <0.05 | 1 | 8.04 | 21.71 |

TABLE 19

Pair wise comparison of the paste formulations show that when Sig = 1 the means difference is significant at the 0.05 level.

| | MeanDiff | SEM | q Value | Prob | Sig | LCL | UCL |
|---|---|---|---|---|---|---|---|
| MFP-Toothboost | −3.29 | 2.05 | 2.27 | 0.13 | 0 | −7.59 | 1.01 |
| MFP-Water | −8.20 | 2.29 | 5.07 | <0.05 | 1 | −13.01 | −3.39 |
| Toothboost-Water | 4.91 | 2.22 | 3.13 | 0.04 | 1 | 0.25 | 9.57 |

7.0 Conclusion

The result of the microindentation and luminescence study shows that when erosive lesion in bovine enamel are treated with either 500 ppm fluoride solution or Toothboost for seven days there is a significant remineralisation compared to a treatment of deionised water (negative control). The negative control group showed some remineralisation which is due to the incubation in artificial saliva, part of the experimental procedure. Microindentation found that Toothboost gave significantly more remineralisation (p=0.05) compared to 500 ppm fluoride whereas luminescence found the two to be statistically the same. A comparison of the individual re-hardening values for the two types of measurements showed a similarity in the change in mineralisation for each of the enamel specimens. Microindentation standard deviation across all samples was 8.23 and luminescence standard deviation was 22.82.

The Calcivis luminescence imaging system was found to be sufficiently sensitive to quantitatively measure free calcium in the intra molecular pores within enamel lesions. The quantification of the calcium had a direct relationship to the degree of enamel mineralisation. Although there was a greater standard deviation of the measurements, compared to microindentation, the author anticipates that this will be improved with further development of this particular method and sample preparation.

The remineralisation performance of the enamel lesions treated with fluoride and Toothboost after seven days were similar. The measurements using the luminescence method suggested they were statistically the same and microindentation suggested they were similar with a probability of being statistically different p=0.05, i.e. 95%. It appears that this is because of the length of time of the re-mineralisation procedure after the initial (and only) acid challenge. It is likely that after the first treatment cycle there is an initial rapid re-mineralisation phase. This is followed by a steadier process of re-mineralisation and at this stage both treatments may reach similar levels of re-mineralisation. Future studies may incorporate regular acid challenges in the method to reflect more the in vivo situation and also help to deconvolute the re-mineralisation capabilities of different formulations.

The "Toothboost" formulation used in the above method was prepared as follows:

TABLE 20

Intermediate A: Preservative/flavour system

| Compound | COSHH | Target/g |
|---|---|---|
| Sodium Methyl Paraben | Irritant | 0.50 |
| Phenoxyethanol | Irritant | 2.00 |
| Saccharine | | 0.80 |

TABLE 20-continued

Intermediate A: Preservative/flavour system

| Compound | COSHH | Target/g |
|---|---|---|
| Tego Betain | | 2.83 |
| Deionised water | | 8.87 |
| Flavour oil | | 5.00 |
| | | 20.00 |

TABLE 21

Intermediate B: Stock solutions

| Compound | COSHH | Target g/500 ml |
|---|---|---|
| Trisodium phosphate 100 mM solution (500 ml) | | 19.00 |
| Disodium hydrogen phosphate 100 mM solution (500 ml) | | 13.40 |
| Calcium chloride (100 ml 1M) | | 14.70 |

TABLE 22

Finished Product

| Compound | % w/w | Target/g |
|---|---|---|
| OPN-10 | 3.00 | 3.00 |
| Trisodium phosphate 100 mM solution | 16.00 | 16.00 |
| Disodium hydrogen phosphate 100 mM solution | 16.00 | 16.00 |
| Deionised water. Add 40 ml in OPN and 10 ml for MFP | 50.00 | 50.00 |
| calcium chloride 1M solution | 2.87 | 2.87 |
| MFP | 0.00 | 0.00 |
| xylitol | 5.00 | 5.00 |
| Intermediate A | 2.00 | 2.00 |
| make up to with water after final pH adjustment | 5.13 | 5.13 |
| Total | 100.00 | 100.00 |

Procedure:
1. To make the Intermediate A:
   Add 5.0 g flavour oil to 2.0 g Phenoxyethanol and mix to a clear solution.
   Add 2.83 g Tego Betaine and 8.87 ml water and mix to a clear solution.
   Add 0.8 g saccharin.
   Add 0.5 g sodium methyl paraben and mix until a clear solution.
   This is a ×10 concentration stock solution.
2. To make the finished product C: Add 50.0 g of deionised water to beaker and add 3.0 g of OPN-10 and rapidly mix until the solution clears.
3. Add 2.87 g calcium chloride (at 1.0 ml/min) with rapid stirring.
4. Adjust the pH of the solution to 9.0 with 1M sodium hydroxide and maintain the pH at this value during the manufacturing procedure.
5. Add tri-sodium phosphate and di-sodium hydrogen phosphate (at 1.0 ml/min) to the OPN-10 solution.
6. Add 2.0 g of intermediate A to the OPN solution at 500 ul/min with rapid stirring. Result is a clear solution.
7. Mix in 5 g xylitol.
8. Adjust the pH of the solution to 8.0 with 1M sodium hydroxide.
9. Make up to 100.0 g with deionised water.
10. After 24H Filter through a 0.22 um sterile filter.

Example 8—OPN Formulation with Tris-HCL Buffer System (Formulation MOH)—3% OPN-10, 28.821 mM Ca, with Extra Buffer The following formulation was produced to demonstrate the use of an alternative buffer system, Tris-HCL. The formulation was successful and the composition demonstrated stable pH. The formulation details are as follows:

TABLE 23

Intermediate A: Preservative/flavour system

| Compound | COSHH | Target/g |
|---|---|---|
| Sodium Methyl Paraben | Irritant | 0.50 |
| Phenoxyethanol | Irritant | 2.00 |
| Saccharine | | 0.80 |
| Tego Betain | | 2.83 |
| Deionised water | | 8.87 |
| Flavour oil | | 5.00 |
| Total | | 20.00 |

TABLE 24

Intermediate B: Stock solutions

| Compound | Target g/500 ml |
|---|---|
| Trisodium phosphate 0.2M solution (500 ml) | 95.00 |
| Disodium hydrogen phosphate 0.2M solution (500 ml) | 67.00 |
| Calcium chloride (100 ml 1M) | 14.70 |

TABLE 25

Finished Product

| Compound | % w/w | Target/g |
|---|---|---|
| OPN-10 | 3.00 | 3.00 |
| Tris buffer (1M) | 16.00 | 16.00 |
| Trisodium phosphate 0.2M solution | 8.00 | 8.00 |
| Disodium hydrogen phosphate 0.2M solution | 8.00 | 8.00 |
| Deionised water. Add 36.75 ml in OPN and 10 ml for MFP | 54.75 | 54.75 |
| calcium chloride 1M solution | 2.87 | 2.87 |
| MFP | 0.38 | 0.38 |
| xylitol | 5.00 | 5.00 |
| Intermediate A | 2.00 | 2.00 |
| make up to with water after final pH adjustment | 0.00 | 0.00 |
| Total | 100.00 | 100.00 |

Procedure:
1. To make the Intermediate A: Add 5 g flavour oil to 2 g Phenoxyethanol and mix to a clear solution.
   Add 2.83 g Tego Betaine and mix to a clear solution.
   Add 8.87 ml water and mix to a clear solution.
   Add 0.8 g saccharin.0.5 g sodium methyl paraben and mix until a clear solution.
   This is a concentration stock solution.
2. To make the finished product C: Add 36.75 g deionised water to beaker and add 3.0 g of OPN-10 and rapidly mix until the solution clears for two hours.
3. Add 1M calcium chloride (1.0 ml/min) with rapid stirring.
4. Adjust the pH of the solution to 7.5 with 1M sodium hydroxide and maintain the pH at this value during the addition of the phosphates.
5. Add tri-sodium phosphate and di-sodium hydrogen phosphate (0.5 ml/min) to the OPN-10 solution with rapid stirring.

6. Add Tris buffer (0.2 ml/min) with rapid stirring.
7. Add 2 ml of intermediate A to the OPN solution at 500 ul/min with rapid stirring. Result is a clear solution.
8. Mix in 5 g xylitol.
9. Add MFP solution.
10. Adjust the pH of the solution to 7.5 with 1M sodium hydroxide.
11. Make up to 100 ml with deionised water.
12. After 24 h filter through a 0.22 um sterile filter.

Formulating Toothboost with 0.16M Tris buffer had a stabilising effect on the formulation maintaining the pH of the formulation above 7.2 (currently) for over 3 months under accelerated storage conditions (40° C./75% relative humidity). Increasing the concentration of phosphates in the current formulation may be undesirable as it could drive the formation of the least soluble molecule, calcium phosphate, by Le Chatelier's Principle.

Another approach for increasing the buffering capacity of the formulation is to use a non-phosphate type buffer so that the calcium phosphate interaction could be minimised. The choice of buffers that have an effective buffering capacity around pH7.5 is limited and of these, two were chosen: tris(hydroxymethyl)aminomethane (Tris), pKa 8.97, buffer range 7.5-9.5 and sodium bicarbonate pKa of 6.1, buffer range 5.1-8.0.

Example 9—OPN Formulation with Sodium Bicarbonate Buffer System (Formulation MOJ)

The following formulation was produced to demonstrate the use of an alternative buffer system, sodium bicarbonate. The formulation was successful and the composition demonstrated stable pH. The formulation details are as follows:

TABLE 26

Intermediate A: Preservative/flavour system

| Compound | COSHH | Target/g |
|---|---|---|
| Sodium Methyl Paraben | Irritant | 0.10 |
| Phenoxyethanol | Irritant | 2.00 |
| Saccharine | | 0.80 |
| Tego Betain | | 2.83 |
| Deionised water | | 9.27 |
| Flavour oil | | 5.00 |
| Total | | 20.00 |

TABLE 27

Intermediate B: Stock solutions

| Compound | Target g |
|---|---|
| Trisodium phosphate 100 mM solution (500 ml) | 19.00 |
| Disodium hydrogen phosphate 100 mM solution (500 ml) | 13.40 |
| Calcium chloride (100 ml 1M) | 14.70 |
| Sodium bicarbonate (100 ml 1M) | 8.40 |

TABLE 28

Finished Product

| Compound | % w/w | Target/g |
|---|---|---|
| OPN-10 | 3.00 | 3.00 |
| Trisodium phosphate 100 mM solution | 16.00 | 16.00 |
| Disodium hydrogen phosphate 100 mM solution | 16.00 | 16.00 |
| Sodium bicarbonate | 10.00 | 10.00 |
| Deionised water. | 41.62 | 41.62 |
| calcium chloride 1M solution | 2.87 | 2.87 |
| MFP | 0.38 | 0.38 |
| xylitol | 5.00 | 5.00 |
| Intermediate A | 2.00 | 2.00 |
| make up to 100 g with water after final pH adjustment | 3.13 | 3.13 |
| Total | 100.00 | 100.00 |

Procedure:
1. To make the Intermediate A: Add 5.0 g flavour oil to 2 ml Phenoxyethanol and mix to a clear solution.
   Add 2.83 g Tego Betaine and mix to a clear solution.
   Add 9.27 ml water and mix to a clear solution.
   Add 0.8 g saccharin.
   0.1 g sodium methyl paraben and mix until a clear solution.
   This is a concentration stock solution.
2. To make the finished product C: Add deionised water to beaker and add 3.0 g of OPN-10 and rapidly mix until the solution clears for two hours.
3. Add 1M calcium chloride (1.0 ml/min) with rapid stirring.
4. Add sodium bicarbonate solution (0.5 ml/min)
5. Adjust the pH of the solution to 7.5 with 1M sodium hydroxide and maintain the pH at this value during the addition of the phosphates.
6. Add tri-sodium phosphate and di-sodium hydrogen phosphate (0.5 ml/min) to the OPN-10 solution.
7. Add 2.0 g of intermediate A to the OPN solution at 500 ul/min with rapid stirring. Result is a clear solution.
8. Mix in 5 g xylitol.
9. Add MFP solution (0.5 ml/min)
10. Adjust the pH of the solution to 7.5 with 1M sodium hydroxide.
11. Make up to 100 g with deionised water.
12. After 24 h filter through a 0.22 um sterile filter.

Formulating Toothboost with 0.1M bicarbonate buffer also shows promise in stabilising the pH of the solution. At present, there is limited stability data to make a definitive formulation choice, but assuming that the bicarbonate buffer works as well as the Tris buffer, the bicarbonate system would probably be a better choice based on cost of goods and product acceptability.

It should be noted that formulations can also be prepared according to the present invention using other calcium phosphate-stabilising agents. In particular, other phosphopeptides, such as casein phosphopeptides, can be effectively for substituted the OPN used in the above examples.

The above examples describe certain preferred embodiments of the invention. It will be apparent that various modifications can be made without departing from the scope of the invention, which is defined in the accompanying claims.

The invention claimed is:

1. A meth of preparing an oral care product having as a constituent thereof a liquid composition comprising soluble or at least a metastable stabilised amorphous calcium phosphate and fluoride, the method comprising:
   a) providing monofluorophosphate, a source of calcium ions, a source of phosphate ions, and a calcium phosphate stabilising agent, wherein the calcium phosphate stabilising agent comprises full length osteopontin and/or a long N-terminal fragment of osteopontin:
b) mixing said source of calcium ions and said source of phosphate ions together with the calcium phosphate stabilising agent in a liquid medium in order to form a stabilised amorphous calcium phosphate complex;
c) mixing the monofluorophosphate with the source of calcium ions, source of phophate ions, calcium phosphate stabilising agent and/or stabilised amorphous calcium phosphate complex in the liquid medium;
wherein the monofluorophosphate, the source of calcium ions, the source of phosphate ions, and the calcium phosphate stabilising agent are all mixed together in a single reaction where precipitation is prevented;
wherein the monofluorophosphate is mixed with the source of calcium ions, the source of phosphate ions, and the calcium phosphate stabilising agent before formation of the stabilised calcium phosphate complex has completed or has reached an equilibrium point, thereby producing a liquid composition comprising a soluble or at least a metastable stabilised amorphous calcium phosphate and fluoride; and
incorporating the liquid composition into an oral care product.

2. The method according to claim 1 wherein the monofluorophosphate, source of calcium ions, source of phosphate ions, and calcium phosphate stabilising agent are added to a single reaction vessel with the liquid medium and mixed together and allowed to react together.

3. The method according to claim 1 comprising storing the liquid composition under suitable conditions for monofluorophosphate to decompose to release fluoride into the liquid medium.

4. The method according to claim 1 wherein the source of calcium ions is a soluble calcium salt.

5. The method according to claim 1 wherein the source of calcium ions is calcium chloride.

6. The method according to claim 1 wherein the source of phosphate ions is a soluble phosphate salt.

7. The method according to claim 1 wherein the source of phosphate ions is sodium phosphate.

8. The method according to claim 1 wherein the liquid medium is water.

9. The method according to claim 1 wherein the final pH of the liquid composition is greater than 7.

10. The method according to claim 1 comprising adding one or more of the following: a pH buffering agent, alcohol, humectant, surfactant, preservative, flavouring agent, cooling agent, sweetening agent, colouring agent, and anti-caries agent.

11. The method according to claim 1 wherein the oral care product is an oral spray or mouthwash.

12. The method according to claim 4 wherein the calcium salt is a calcium salt having a solubility of 5 g of salt per 100 ml of liquid medium or higher.

13. The method according to claim 4 wherein the calcium salt is a calcium salt having a solubility of 10 g of salt per 100 ml of liquid medium or higher.

14. The method according to claim 4 wherein the calcium salt is a calcium salt having a solubility of 50 g of salt per 100 ml of liquid medium or higher.

15. The method according to claim 1 wherein the source of phosphate ions is a soluble phosphate salt having a solubility of 5 g of salt per 100 ml of liquid medium or higher.

16. The method according to claim 1 wherein the source of phosphate ions is a soluble phosphate salt having a solubility of 10 g of salt per 100 ml of liquid medium or higher.

17. The method according to claim 1 wherein the source of phosphate ions is a soluble phosphate salt having a solubility of 50 g of salt per 100 ml of liquid medium or higher.

18. The method according to claim 1 wherein the source of phosphate ions is disodium hydrogen phosphate and/or trisodium phosphate.

19. The method according to claim 1, wherein the calcium phosphate stabilising agent is a mixture comprising full length osteopontin and the long N-terminal fragment of osteopontin.

20. The method according to claim 19, wherein the calcium phosphate stabilising agent is a mixture comprising 5-40% (w/w) full length osteopontin and 60-95% (w/w) of the long N-terminal fragment of osteopontin.

* * * * *

UNITED STATES PATENT AND TRADEMARK OFFICE
CERTIFICATE OF CORRECTION

PATENT NO. : 12,109,284 B2
APPLICATION NO. : 16/347948
DATED : October 8, 2024
INVENTOR(S) : David Andrew Smillie and Richard James Willson Page 1 of 1

It is certified that error appears in the above-identified patent and that said Letters Patent is hereby corrected as shown below:

In the Claims

Column 32, Line 61 (Claim 1): Change "A meth" to -- A method --.

Signed and Sealed this
Fourteenth Day of January, 2025

Derrick Brent
*Acting Director of the United States Patent and Trademark Office*